US009901407B2

(12) United States Patent
Breisacher et al.

(10) Patent No.: US 9,901,407 B2
(45) Date of Patent: Feb. 27, 2018

(54) COMPUTER-IMPLEMENTED TECHNIQUE FOR DETERMINING A COORDINATE TRANSFORMATION FOR SURGICAL NAVIGATION

(71) Applicant: Stryker Leibinger GmbH & Co. KG, Freiburg (DE)

(72) Inventors: Jochen Breisacher, Teningen (DE); Jean Stawiaski, Kirchzarten (DE); Tobias Reiff, Freiburg (DE)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 22 days.

(21) Appl. No.: 14/905,690

(22) PCT Filed: Aug. 23, 2013

(86) PCT No.: PCT/EP2013/067529
§ 371 (c)(1),
(2) Date: Jan. 15, 2016

(87) PCT Pub. No.: WO2015/024600
PCT Pub. Date: Feb. 26, 2015

(65) Prior Publication Data
US 2016/0157938 A1  Jun. 9, 2016

(51) Int. Cl.
*A01B 19/00* (2006.01)
*A61B 34/20* (2016.01)
(Continued)

(52) U.S. Cl.
CPC ............ *A61B 34/20* (2016.02); *G06F 19/321* (2013.01); *G06F 19/3437* (2013.01);
(Continued)

(58) Field of Classification Search
None
See application file for complete search history.

(56) References Cited

U.S. PATENT DOCUMENTS 6,033,415 A   3/2000 Mittelstadt et al.
6,381,485 B1 * 4/2002 Hunter ................. G06T 3/0068
                                                              324/244
(Continued)

FOREIGN PATENT DOCUMENTS

EP   2153794 A2   2/2010
EP   2452649 A1   5/2012
(Continued)

OTHER PUBLICATIONS

Klein, Georg; Murray, David: "Parallel Tracking and Mapping for Small AR Workspaces"; Active Vision Laboratory Department of Engineering Science, University of Oxford; 2007 ISMAR.
(Continued)

*Primary Examiner* — Delomia L Gilliard
(74) *Attorney, Agent, or Firm* — Howard & Howard Attorneys PLLC

(57) ABSTRACT

A technique for determining a transformation between a navigation reference coordinate system (302) for navigation of a surgical device (150) relative to patient image data and an image coordinate system (304) in which the patient image data define a shape of a patient surface is provided. A computer-implemented method implementation of that technique comprises receiving multiple data sets that have been taken from different perspectives of the patient surface. Feature coordinates of multiple features (170) identifiable in the picture data sets are determined from the picture data sets and in the navigation reference coordinate system (302). From the feature coordinates, a shape model of the patient surface in the navigation reference coordinate system (302) is determined. Then, surface matching between the shape model and the shape of the patient surface defined by the patient image data is applied to determine the transformation
(Continued)

(T1) between the navigation reference coordinate system (302) and the image coordinate system (304).

34 Claims, 15 Drawing Sheets

(51) Int. Cl.
*G06F 19/00* (2018.01)
*A61B 90/00* (2016.01)
*A61B 34/10* (2016.01)

(52) U.S. Cl.
CPC . *A61B 2034/105* (2016.02); *A61B 2034/2055* (2016.02); *A61B 2034/2065* (2016.02); *A61B 2090/364* (2016.02); *A61B 2090/367* (2016.02)

(56) References Cited

U.S. PATENT DOCUMENTS

| | | |
|---|---|---|
| 6,978,167 B2 | 12/2005 | Dekel et al. |
| 8,457,719 B2 | 6/2013 | Moctezuma de la Barrera et al. |
| 2004/0147839 A1* | 7/2004 | Moctezuma de la Barrera ........ A61B 34/20 600/429 |
| 2004/0257444 A1* | 12/2004 | Maruya ............ G08B 13/19645 348/169 |
| 2005/0283048 A1* | 12/2005 | Gill .................... A61B 1/00059 600/121 |
| 2007/0018975 A1* | 1/2007 | Chuanggui ............ A61B 90/36 345/419 |
| 2007/0238981 A1* | 10/2007 | Zhu ........................ A61B 90/36 600/424 |
| 2008/0208041 A1* | 8/2008 | Gilboa .................... A61B 6/12 600/426 |
| 2008/0269588 A1* | 10/2008 | Csavoy ................. A61B 34/20 600/407 |
| 2009/0262979 A1* | 10/2009 | Markowitz .......... A61B 5/0422 382/103 |
| 2011/0270084 A1* | 11/2011 | Choi ........................ G06T 7/33 600/427 |
| 2013/0245461 A1* | 9/2013 | Maier-Hein ......... A61B 5/0035 600/476 |
| 2014/0105486 A1* | 4/2014 | Tamaazousti ........... G06T 7/579 382/154 |
| 2014/0275763 A1* | 9/2014 | King .................. A61B 1/00022 600/103 |
| 2015/0351860 A1* | 12/2015 | Piron ..................... A61B 90/90 600/417 |

FOREIGN PATENT DOCUMENTS

| | | |
|---|---|---|
| WO | 2011063266 A2 | 5/2011 |
| WO | 2011130567 A2 | 10/2011 |
| WO | 2011134083 A1 | 11/2011 |
| WO | 2012169990 A2 | 12/2012 |

OTHER PUBLICATIONS

Kletter, R.: "Surface from Motion-without and with Calibration"; Theoretical Foundations of Computer Vision; Computing Supplement vol. 11, 1996, pp. 73-98.

Flöry S., Hofer M: "Surface Filling and Registration of Point Clouds using Approximations of the Unsigned Distance Function", Computer Aided Geometric Design (CAGD), 2010.

Aigner D., Mitra NJ., Cohen-Or D.: "4-Points Congruent Sets for Robust Pairwise Surface Registration" ACM Trans. Graphics, 27/3, Proc. SIGGRAPH, 2008.

Mika Niloy J. et al.: "Dynamic Geometry Registration" Symposium on Geometry Processing, 2007.

Huang Q.-x. et al.: "Reassembling fractured objects by geometric matching", ACM Trans. Graphics., Proc. SIGGRAPH 2006.

Pottmann H. et al: "Geometry and convergence analysis of algorithms for registration of 3D shapes", Int. J. Computer Vision.

Gelfand N. et al.: "Robust global registration", in M. Desbrun and H. Pottmann, editors, SGP 2005: Third Eurographics Symposium on Geometry processing.

International Search Report for Application No. PCT/EP2013/067529 dated Jun. 27, 2014, 19 pages.

* cited by examiner

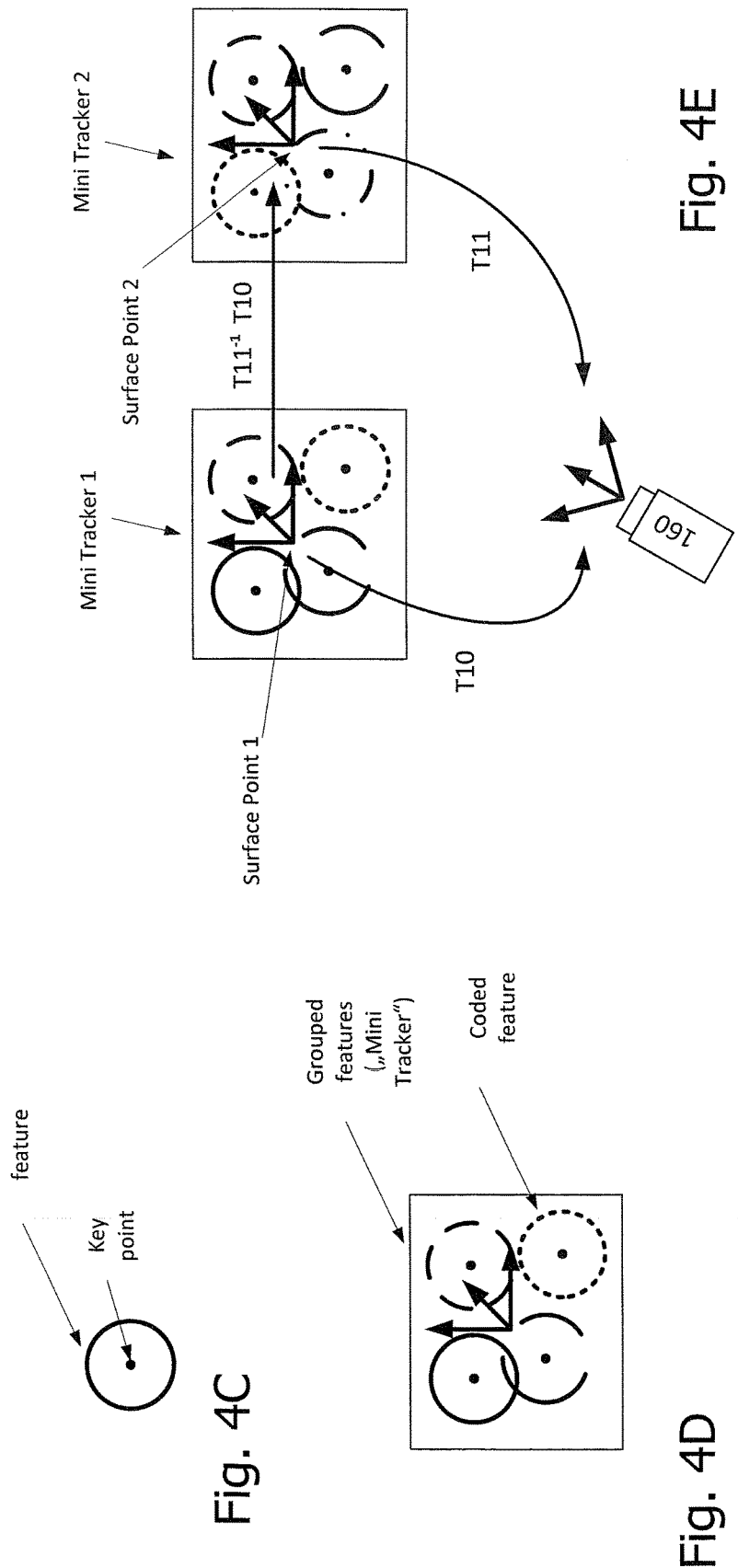

COMPUTER-IMPLEMENTED TECHNIQUE FOR DETERMINING A COORDINATE TRANSFORMATION FOR SURGICAL NAVIGATION

CROSS-REFERENCE TO RELATED APPLICATIONS

This application is the National Stage of International Patent Application No. PCT/EP2013067529, filed on Aug. 23, 2013, the content of which is incorporated herein by reference.

TECHNICAL FIELD

The present disclosure generally relates to computer-assisted surgery. Specifically, a technique is presented for determining a transformation between a navigation reference coordinate system and an image coordinate system. The technique can be implemented as a method, a computer program, a device and a system.

BACKGROUND

The number of surgical procedures performed under assistance from surgical navigation systems has tremendously increased over the last decade. This increase can in part be attributed to the fact that surgical navigation systems have become less complex in use and construction.

Surgical navigation is typically performed on the basis of patient image data (e.g., a Computerized Tomography, or CT, scan) acquired either prior to surgery or intra-operatively. For image-guided surgery the current position of a surgical device relative to the patient is superimposed on the patient image and visualized. The superposition requires registering a navigation reference coordinate system (in which a relative movement between the surgical device and the patient is tracked) with respect to an image coordinate system (in which the patient image data are provided). From a mathematical perspective, the registration involves the calculation of a transformation between the navigation reference coordinate system and the image coordinate system.

After successful registration, the relative movement between a navigated surgical device and the patient can be tracked and visualized. Tracking is performed using a tracking camera configured to detect one or more tracking devices within its field of view. Conventionally, both the patient and the surgical device are each associated with a dedicated tracking device. Such a navigation approach is known, for example, from U.S. Pat. No. 8,457,719 B2 to Stryker Corporation.

U.S. Pat. No. 8,457,719 B2 discloses a tool tracking device and a patient tracking device that each comprise multiple spaced apart tracking points in the form of Light Emitting Diodes, LEDs. The patient tracking device comprises a flexible patch with an adhesive layer on one side to be stuck on to the patient such that the tracking points provided on the opposite side of the patch conform to the patient surface.

The tracking points on the patient tracking device and those on the tool tracking device are detectable by a tracking camera comprised of three separate Charge-Coupled Device (CCD) camera arrays. The tracking camera is mounted to a cart, an operating room wall or an operating room light.

For registration purposes, a model of a patient surface is constructed to which the patient tracking device is stuck on. Construction of the surface model requires localizing the tracking points on the patient tracking device by the tracking camera. In this regard a registration routine instructs the surgeon to move the patient one or multiple times until sufficient tracking points are within the field of view of the tracking camera. As will be appreciated, the quality of the surface model strongly depends on the number of tracking points that can be accurately detected.

Once a reliable surface model has been constructed from the detected tracking points, that surface model is registered to patient image data in the form of a CT scan. The registration can be performed using surface matching techniques. If the scanned patient image and the shape model can be registered within a predetermined error level, the registration routine confirms success of the registration procedure. Success of the registration procedure is strongly influenced by the quality of the surface model. The quality of the surface model, in turn, depends on the number of tracking points accurately detected by the tracking camera.

There also exist navigation approaches in which only the patient is tracked, while the position of the surgical device is calculated relative to the patient tracking device using a priori knowledge about the surgical device and the tracking camera. In this regard, US 2008/0208041 A1 to Activiews Ltd. teaches a surgical navigation system with a patient tracking device in the form of a substantially planar patch that is configured to be applied to a patient. The patch includes an optically detectable tracking point arrangement and an additional radio-opaque fiducial arrangement with a known spatial relationship relative to the tracking point arrangement.

Registration between a pre-operatively taken CT scan and the patient is done by matching the radio-opaque fiducial arrangement identified in the CT scan with the tracking point arrangement detected by a tracking camera attached to the surgical device. During surgical navigation, that device-mounted tracking camera tracks the tracking point arrangement and calculates a position of the surgical device relative to the tracking point arrangement based on knowledge about the geometry of the surgical device, the geometry of the tracking point arrangement and the imaging properties of the tracking camera. As such, there is no need for a separate tool tracking device.

SUMMARY

It is an object of the present disclosure to improve registration performance.

According to one aspect, a computer-implemented method is provided of determining a transformation between a navigation reference coordinate system for navigation of a surgical device relative to patient image data and an image coordinate system in which the patient image data define a shape of a patient surface. The method comprises receiving multiple picture data sets, wherein the picture data sets have been taken from different perspectives of the patient surface. The method further comprises determining, from the picture data sets and in the navigation reference coordinate system, feature coordinates of multiple features identifiable in the picture data sets, determining, from the feature coordinates, a shape model of the patient surface in the navigation reference coordinate system, and determining a transformation between the navigation reference coordinate system and the image coordinate system using surface matching between the shape model and the shape of the patient surface defined by the patient image data.

The method may be performed during a registration procedure that precedes the actual navigation procedure. As will be appreciated, the resulting registration can be updated or verified, so that the method presented herein may also be practiced concurrently with the navigation procedure.

The steps of the method presented herein may be performed by a computer device. The computer device may be comprised by a system for computer-assisted surgery. In particular, the method steps may be performed using at least one of hardware and software components. As an example, the receiving step may be performed by at least one of a hardware and a software interface, and the determining steps may be performed by one or more processors (e.g., under software control) coupled to the interface.

The picture data sets may be received from a first camera. The first camera may be movable relative to the patient upon taking the picture data sets. In one variant, the first camera is a video camera. In such a case, the picture data sets may be received from the first camera in the form of a video data stream (e.g., as video frames). The first camera may be a non-stereoscopic camera (e.g., it may provide for a given point in time a single picture data set from a single perspective).

The first camera may be a handheld camera. Alternatively, or in addition, the first camera may be attachable to the surgical device. The surgical device may be a handheld device. For example, the surgical device may take the form of a surgical tool, such as a surgical pointer, a surgical needle (e.g., a biopsy needle) or a surgical power tool.

The features identifiable in the picture data sets may be grouped to form one or more feature groups. To each feature group at least one of a position and an orientation may be attributable. There may exist a priori knowledge about the groupings (e.g., as to which features define which feature group in terms of a known feature coding scheme). It should be noted that a feature group may again be regarded as a feature of its own with specific feature coordinates (e.g., of a feature group center).

According to one implementation, at least one of the feature coordinates and the shape model is determined using one or more of a Structure-from-Motion (SfM) technique, a Simultaneous Localization and Mapping (SLAM) technique and a pose estimation technique. As an example, SLAM may be applied to the feature groups. As a further example, SfM may build feature tracks for individual features (not necessarily feature groups) identifiable in the picture data sets from different perspectives. Triangulation based on different (camera) perspectives may be applied to individual feature tracks. Triangulation may help to reconstruct and, optionally, optimize the feature coordinates in three dimensions (e.g., in the navigation reference coordinate system).

The shape model may be determined in the form of a cloud of points lying on, or defining, a surface. The point cloud may comprise 20 and more points (e.g., over 30 or more points). Each point may be represented by the coordinates of a feature (e.g., of a feature key point or of a feature group center).

The navigation reference coordinate system may generally be the coordinate system intended to be used for navigation of the surgical device during surgery (e.g., after successful registration relative to the image coordinate system). As an example, the navigation reference coordinate system may be the coordinate system in which a patient tracking device is tracked for navigation of the surgical device. In one implementation, the surgical device may additionally be tracked in the navigation reference coordinate system using a dedicated tool tracking device. In another implementation, the position of the surgical device, or a portion thereof, may be calculated in the navigation reference coordinate system without use of a tool tracking device.

The navigation reference coordinate system may be determined on the basis of at least some of the features identified in the picture data sets. In one variant, some of the identified features are selected (e.g., during run-time) to define the navigation reference coordinate system. In another variant, a priori knowledge is available that some of the features identified in the picture data sets are arranged to define, or span, the navigation reference coordinate system. In both variants, the identified features may, but need not, be differentiable from each other (e.g., by an appropriate coding). In this way, the robustness of the determination can be increased.

The feature coordinates may be determined for one or more tracker features of a patient tracking device for use during surgical navigation, wherein the patient tracking device is at least partially identifiable in the picture data sets and has a fixed position relative to the patient. The patient tracking device may take various forms, such as a headset, a rigid or flexible patch attachable to a patient surface, or a device attachable to bone. The patient tracking device may comprise a tracker feature arrangement. When practicing the method presented herein, a priori knowledge of the geometric properties of that tracker feature arrangement (e.g., of the relative positions between the individual tracker features) and/or of the (e.g., coded) characteristics of the individual tracker features within the arrangement may be available.

The tracker features may at least partially define the navigation reference coordinate system. In this regard, a priori knowledge regarding how the navigation reference coordinate system is defined by the tracker features may be available. That a priori knowledge may permit determining (e.g., constructing) the navigation reference coordinate system from the positions of the identified tracker features in space and/or their (e.g., coded) characteristics. In certain implementations, instead of or in addition to one or more tracker features, one or more other features identifiable in the picture data sets may be used for defining the navigation reference coordinate system.

Additionally, or as an alternative, the feature coordinates may be determined for one or more anatomic patient features, including skin features, identifiable in the picture data sets. As will be appreciated, the feature coordinates of the one or more anatomic patient features may be identified in addition to or instead of the tracker features. Identifying the one or more anatomic patient features in the picture data sets may be performed using generic knowledge about anatomic features (e.g., as to their expected extension, location and/or shape).

The navigation reference coordinate system may, at least partially, be determined from the anatomic patient features. In this regard, one or more of the identified anatomic patient features may be used to span the navigation reference coordinate system. The navigation reference coordinate system can be solely spanned by the anatomic patient features or by a combination of the anatomic patient features and other features identified in the picture data sets (e.g., one or more tracker features).

In one variant, the shape model is at least partially determined from the anatomic patient features. In such a case, the surface matching may comprise a matching between the patient surface defined by the patient image data with a surface defined by the relative locations of the identified anatomic patient features. Of course, the shape model may also be determined from additional or alternative features identifiable in the picture data sets.

In one implementation, the feature coordinates are determined for one or more patch features of a feature patch applied to the patient and at least partially identifiable in the picture data sets. The feature patch may comprise a substrate that has an essentially planar appearance or, alternatively, be flexible to conform to the patient surface. Alternatively, the feature patch may simply be drawn on the patient's skin and will thus also conform to the patient surface. The shape model may at least partially be determined from the patch features. The shape model may also be determined from a combination of one or more patch features and one or more anatomic patient features.

Generally, the feature patch may take the form of a skin mask for application to the patient. The skin mask may be have a form (e.g., an outer contour) that is tailored to a region of anatomic features of a patient to which the skin mask is intended to be applied (e.g., the forehead or in a region of the cheek bones). In this way the features may selectively be applied to anatomic regions particularly suited for surface matching (e.g., having a characteristic surface).

Also the navigation reference coordinate system may, at least partially, be determined from the patch features. As an example, the navigation reference coordinate system could be determined solely from the patch features or from a combination of one or more patch features and one or more further features identifiable in the picture data sets (such as one or more tracker features and/or one or more anatomic patient features). For determining the navigation reference coordinate system, there may exist a priori knowledge regarding the relative locations and/or (e.g., coded) characteristics of the patch features.

Determination of the navigation reference coordinate system may be based on a scaling factor. The scaling factor may in one implementation be derived from the surface matching. As an example, scaling information provided with the patient image may, in connection with the surface matching, be used to derive a scaling factor for the navigation reference coordinate system. Additionally, or as an alternative, scaling features of a scaling reference identifiable in the picture data sets may be exploited for determine the scaling factor for the navigation reference coordinate system.

The technique presented herein may generally also comprise tracking or calculating, during navigation, a position of the surgical device, or a portion thereof, relative to one or more of the features from which the navigation reference coordinate system has been determined. In this regard, the surgical device may be associated with a tool tracking device detectable by a tracking camera. Alternatively, a tracking camera may be mounted to the surgical device and the position of the surgical device, or a part thereof, may be calculated (e.g., based on a priori knowledge of the geometric relationship between the surgical device, or a device portion, on the one hand and the camera on the other).

The tracking or calculating may be performed based on at least one of one or more anatomic patient features and one or more (artificial) tracker features of the patient tracking device. In sum, at least four features may be used to this end. As to the tracker features, the patient tracking device may be different from a feature patch, in particular a feature patch with a flexible substrate, applied to the patient.

A surgical device, or a portion thereof, may be visualized relative to the patient image. Such a visualization may be adapted in accordance with the tracking or calculating (including estimation) of the position of the surgical device relative to one or more of the features from which the navigation reference coordinate system has been determined. The coordinates of those features are known in the navigation reference coordinate system.

Generally, the picture data sets may be received from a first camera and the tracking or calculating may be performed based on picture information provided by a second camera different from the first camera during navigation. The first camera may be configured to be (e.g., freely) movable within the operating room relative to the patient upon taking the picture data sets. The second camera may be maintained at an essentially fixed location in an operating room during surgery. As an example, the second camera may be mounted to an operating room wall, an operating room light or an essentially stationary cart.

In an alternative implementation, the picture data sets for determining the transformation between the navigation reference coordinate system and the image coordinate system are received from a first camera, and the tracking or calculating is also performed based on the picture data sets received from the first camera during navigation.

The features identifiable in the picture data sets may take various forms. As an example, the features may take the form of three-dimensional bodies or two-dimensional items. The identified features may be differentiable from each other, or may not be distinguishable. In the first case, two or more of the features identifiable in the picture data sets may be coded, or characterized, according to a pre-defined coding scheme so as to be differentiable from each other in the picture data sets. The coding scheme can be a color scheme or a more sophisticated scheme, such as a Quick Response (QR) code-type scheme. In particular in the latter case, the features may also be overlapping.

The features are preferably configured such that they can be associated with, or reduced to, a single point in space (e.g., as coordinates within the navigation reference coordinate system) independently from the perspective from which the picture data sets have been taken. To this end, key point estimation may be performed. The feature coordinates may then be expressed as coordinates of the feature key points or derived from multiple feature key points (e.g., in the case of feature groups).

Pattern recognition technologies can be used for identifying (e.g., locating) one or more of the features in the picture data sets (for example based on a priori knowledge). The pattern recognition technologies may also allow differentiating the identified features from each other. Also here, a priori knowledge may be used.

In one implementation the method presented herein further comprises receiving image data of the imaged patient. The patient image data may be provided for two or three dimensions. A three-dimensional patient image may also be referred to as image volume. The image data are preferably provided in the image coordinate system.

The method may also comprise the step of extracting the shape of the patient surface from the image data. In this regard, a predefined or arbitrary portion of the patient contained in the image data may be used for shape extraction. The shape extraction may result in a point cloud defining the patient surface.

The image data may take various forms. As an example, the image data may be provided as ultrasound data or in the form of a CT scan, in the form of a Magnetic Resonance Tomography (MRT) scan or in the form of a Positron Emission Tomography (PET) scan. The image data may also define the image coordinate system.

The patient image data may not show any registration marker (such as radio-opaque fiducials). In other words, the surface matching may in certain variants be used to eliminate the need for associating registration markers with the patient prior to image data acquisition. The patient image data may be generated pre-operatively. Alternatively, or in addition, image data provided during surgery may be used.

The registration transformation may be determined prior to navigation. Additionally, the transformation may be determined anew or adjusted one or more times during navigation (e.g., to verify or correct the transformation determined prior to navigation). In this way, registration may be repeated one or more times to increase navigation accuracy. In one implementation, the transformation is determined anew based on each picture data set received during navigation. In this regard, a filtering approach may be implemented. As an example, the transformation may be determined from a predetermined number of picture data sets that always includes the newest picture data set received during navigation.

Also provided is a computer program product comprising program code portions for performing the steps of any of the methods and method aspects described herein when the computer program product is executed by a computing device. The computer program product may be stored on a computer-readable recording medium, such as a hard disk, CD-ROM, DVD or semiconductor memory. Also, the computer program product may be provided for download via a network connection.

According to a further aspect, a device is provided for determining a transformation between a navigation reference coordinate system for navigation of a surgical device relative to patient image data and an image coordinate system in which the patient image data define a shape of a patient surface. The device comprises an interface adapted to receive multiple picture data sets, wherein the picture data sets have been taken from different perspectives of the patient surface. The device further comprises a processor adapted to determine, from the picture data sets and in the navigation reference coordinate system, feature coordinates of multiple features identifiable in the picture data sets, to determine, from the feature coordinates, a shape model of the patient surface in the navigation reference coordinate system, and to determine a transformation between navigation reference coordinate system and the image coordinate system using surface matching between the shape model and the shape of the patient surface defined by the patient image data.

Additionally provided is a system for computer-assisted surgery. The system comprises the device presented herein as well as a camera. The camera may be configured to be movable relative to the patient and to provide the picture data sets.

BRIEF DESCRIPTION OF THE DRAWINGS

Further aspects, details and advantages of the present disclosure will become apparent from the following description of exemplary embodiments in conjunction with the accompanying drawings, wherein:

FIGS. 4C-4E schematically illustrate the concepts of feature key points and trackable feature groups.

DETAILED DESCRIPTION

In the following description of exemplary embodiments, for purposes of explanation and not limitation, specific details are set forth, such as particular methods, functions and procedures, in order to provide a thorough understanding of the technique presented herein. It will be apparent to one skilled in the art that this technique may be practiced in other embodiments that depart from these specific details. For example, while the following embodiments will primarily be described on the basis of registration and navigation scenarios pertaining to ENT (ear, nose, throat) surgery and neurosurgery, it will be evident that the technique presented herein could also be implemented with respect to other regions of a patient's body, for example for spinal surgery.

Moreover, those skilled in the art will appreciate that the methods, functions and steps explained herein may be implemented using software functioning in conjunction with the programmed microprocessor, an Application Specific Integrated Circuit (ASIC), a Digital Signal Processor (DSP) or general purpose computer. It will also be appreciated that while the following embodiments will primarily be described in the context of methods, systems and devices, the present disclosure may also be embodied in a computer program product which can be loaded to run on a computing device or a distributed computer system comprising one or more processors and one or more memories functioning as a storage, wherein the one or more memories are configured to store one or more computer programs that control the one or more processors to perform the methods, functions and steps disclosed herein.

Figure 1A:
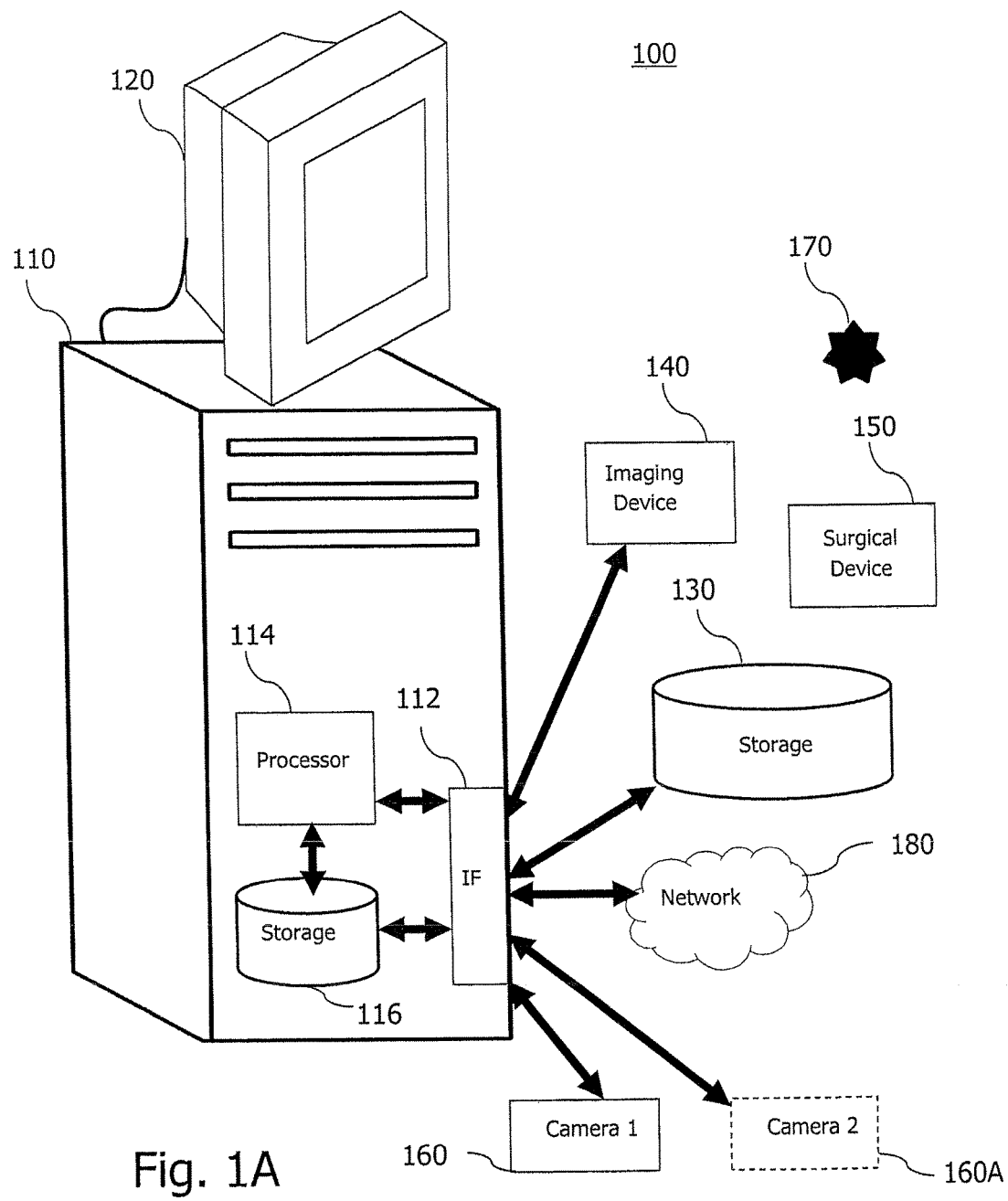
FIG. 1A schematically illustrates an embodiment of a system for computer-assisted surgery capable of determining a transformation between a navigation reference coordinate system and an image coordinate system.

FIG. 1A illustrates an embodiment of a system 100 for computer-assisted surgery. As illustrated in FIG. 1A, the system 100 comprises a computing device 110 (such as a personal, tablet or laptop computer), a display device 120 (such as a touchscreen or computer monitor), and an external storage 130 (such as a hard disk or semiconductor memory in which a database or other data system is provided). The system 100 also includes an imaging device 140 configured to take image data of a patient region in two or three dimensions. Generally, the imaging device 140 could be a free-hand operable device, a mechanically guided device or a fully stationary device. As an example, the imaging device 140 may be a CT device, an MRT device, a PET device or an ultrasound device. The imaging device 140 is configured to provide the patient image data in accordance with the Digital Imaging and Communication in Medicine (DICOM) format, or any other patient image format, to the computing device 110 (e.g., via a data carrier such as CD-ROM or a wireless or wired link). Alternatively, the computing device 110 or a computing device different therefrom may configured to format the patient image data acquired by the imaging device 140 in accordance with any patient image format.

The system 100 may also comprise at least one user-operable input device such as one or more buttons, a keyboard, a mouse or a trackball (not shown) for generating (or triggering the generation) of user interaction signals. The user interaction signals may control the operation of the system 100. The input device and the display device 120 may be integrated into a touchscreen. The touchscreen, in turn, may be part of a tablet computer.

The system 100 further includes a surgical device 150 (e.g., a surgical tool) for use in a surgical procedure. As understood herein, also diagnostic and therapeutic treatments of a patient are regarded to constitute surgical procedures. The surgical device 150 may comprise the input device (e.g., in the form of one or more buttons).

The surgical device 150 can be a free-hand operable device or a guided device. In the latter case, the surgical device 150 may be operated by a surgical robot (e.g., fully automatically or semi-automatically). In other variants, a mechanical guidance may be present that constrains a movement of the surgical device 150 by a surgeon. In some of the following embodiments, the surgical device 150 is configured as a biopsy needle or on endoscope.

The display device 120 is configured to visualize patient image data. The patient image data have been taken by the imaging device 140 prior to or during the surgical procedure. The display device 120 is further configured to visualize computer-assisted guidance for navigating the surgical device 150 relative to the patient. Such visualization may include superimposing the current position (optionally including the orientation) of the surgical device 150 or a portion thereof on a patient image derived from the image data. It should be noted that such guidance could additionally, or alternatively, be provided via acoustic or haptic feedback.

As shown in FIG. 1A, the system 100 also comprises at least one camera 160 and multiple features that define a feature set 170. The camera 160 is configured to acquire picture data sets of a patient from two or more different perspectives so that each includes at least some of the features of the feature set 170. The camera 160 may be a handheld camera configured to be freely movable relative to a patient upon taking the picture data sets. As an example, the camera 160 may be realized as a video camera capable of providing the picture data sets in the form of a continuous video data stream (e.g., as video frames).

In one variant, the camera 160 is rigidly mounted to the surgical device 150 such that the camera 160 can be moved together with the surgical device 150. In another variant, the camera 160 can be operated independently from the surgical device 150. In such a variant, the camera 160 may be incorporated in a smartphone, tablet computer or any other mobile user equipment.

Optionally, at least one further camera 160A may be provided. In one implementation, the further camera 160A is rigidly mounted to the surgical device 150 to be used for tracking during surgical navigation (e.g., as described in US 2008/0208041 A1), whereas the other camera 160 can be manipulated independently from the surgical device 150 in connection with a registration procedure in which the coordinate system transformation is determined as described herein. In another implementation the camera 160 is rigidly mounted to the surgical device 150 and used for both registration and navigation (i.e., tracking) purposes. In a further implementation, both cameras 160, 160A are mounted to the surgical device 150, wherein the camera 160 is used for registration purposes and the camera 160A is used for guided navigation purposes. In a still further implementation, the camera 160A is used for tracking during surgical navigation and attached to an operating room wall, an operating room light or a cart (not shown in FIG. 1A). The cart may be configured to transport at least the computing device 110 as well as the display device 120.

When mounted to the surgical device 150, any of the cameras 160, 160A may have a field of view that includes a patient surface targeted at by the surgical device 150. As an example, when the surgical device 150 has a longitudinal axis in use directed towards the patient, the field of view may extend along the longitudinal axis of the surgical device 150.

The feature set 170 comprises multiple features that are identifiable at least in the picture data sets taken by the camera 160 (and optionally, the camera 160A). For such identification purposes, pattern recognition capabilities can be provided by the computing device 110. In this regard, the system 100 may or may not have a priori knowledge of the arrangement, coding or other characteristics of the features to be detected. One or more of the features may be active markings (e.g., emitting radiation to be detected by the camera 160). Additionally, or in the alternative, one or more of the features may be passive markings. Passive markings may have reflecting or non-reflecting properties. Passive markings may be realized (e.g., by printing) on any rigid (e.g., planar) or flexible substrate, such as any of the patient and tool tracking devices presented herein, or be painted on the patient's skin. One or more of the features may also be realized by characteristic anatomic patient features that can, but need not, comprise any additional marking.

Figure 1B:
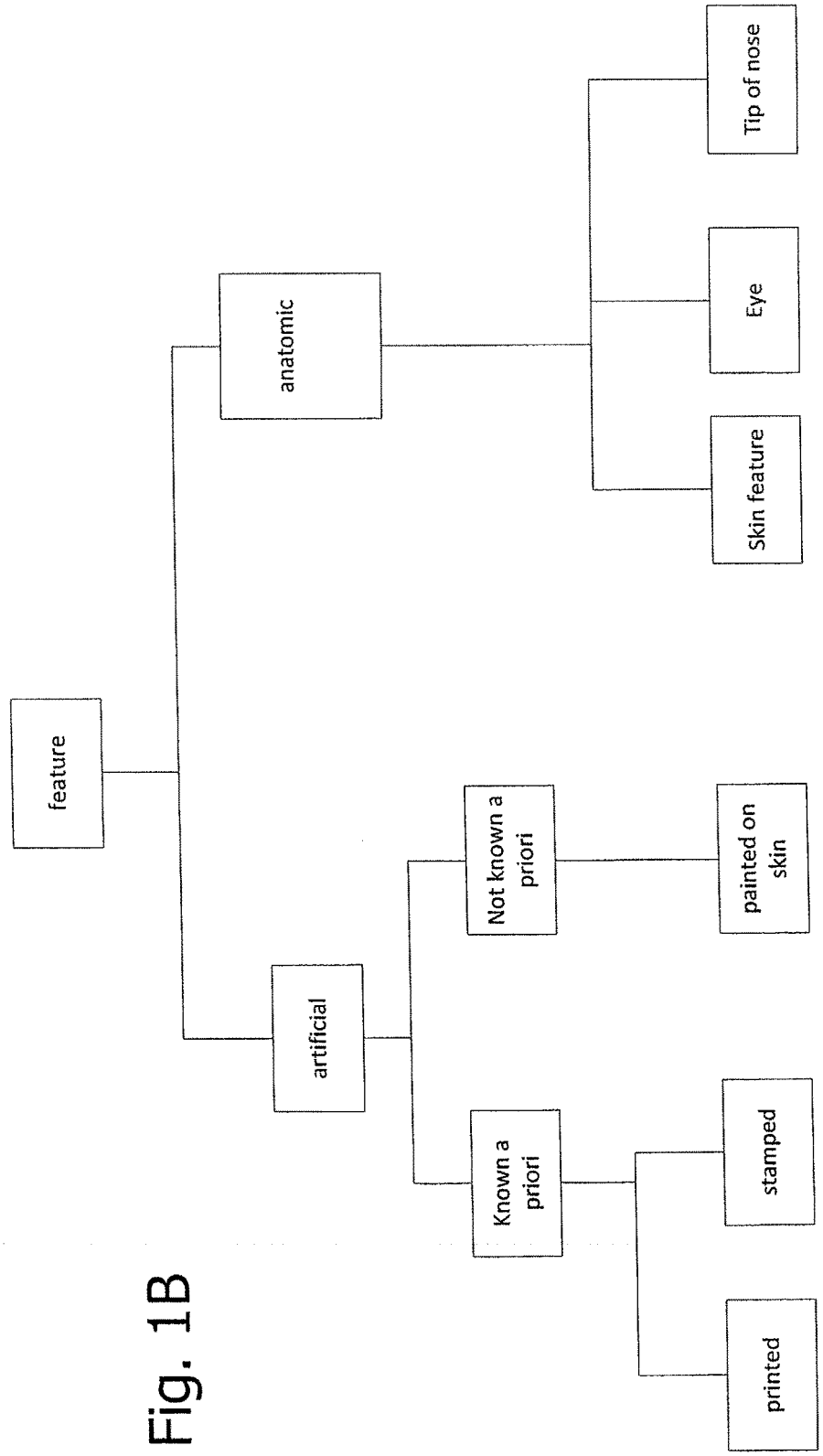
FIG. 1B is a tree diagram explaining various feature embodiments usable in the system embodiment of FIG. 1A.

FIG. 1B illustrates in a tree diagram exemplary feature realizations. As shown therein, the features can either be artificial features or anatomic features. The system 100 may or may not have a priori knowledge of the artificial features (e.g., in the form of so-called calibration information). The a priori knowledge may relate to one or more of a feature coding scheme and positions of the features relative to each other. Artificial features known a priori may, for example, be passive markings stamped or printed on a substrate, or alternatively, active markings (not shown in FIG. 1B). Artificial features not known a priori may be realized by a random painting on a patient's skin.

As to the anatomic features, the system 100 will generally have no dedicated a priori knowledge, but may use generic models to identify same. As examples for anatomic features, (typically two-dimensional) skin features such as freckles, birth marks and pores can be mentioned. Other (typically three-dimensional) anatomic features include, for example, the patient's eyes or tip of the nose.

Now returning to FIG. 1A, the computing device 110 comprises at least one data interface 112, at least one processor 114, such as a Central Processing Unit (CPU), and an internal storage 116 such as a hard disk or a semiconductor memory for storing data and program code. The data interface 112 is in one variant configured as an input/output interface. Generally, the data interface 112 may be used for establishing a wired or wireless communication between the computing device 110 on the one hand and, on the other hand, one or more of the display device 120, the external storage 130, the imaging device 140, the cameras 160, 160A, and a computer network 180 (such as a Local Area Network (LAN), and/or the Internet). The data interface 112 can be realized in the form of one or more hardware components, one or more software components or a combination thereof. As an example, the data interface may be realized to comprise one or more Universal Serial Bus (USB) interfaces. The data interface 112 may alternatively, or additionally, be realized as a device for reading a data carrier (such as a CD-ROM or SD card).

The internal storage 116 or the external storage 130, or both, may be configured to store image data of a patient image taken by the imaging device 140. Alternatively, or in addition, such image data may also be received (e.g., downloaded) via the computer network 180. The external storage 130 may, for example, at least partially be realized in the imaging device 140 for being read by the computing device 110.

Moreover, the internal storage 116 or the external storage 130, or both, may be configured to store various items of calibration data. Such calibration data constitute a priori knowledge of the system 100, and various calibration data examples will be described below in more detail. As will be appreciated, the a priori knowledge of the system 100 may alternatively, or in addition, comprise other items of information.

The internal storage 116 or the external storage 130, or both, may additionally be configured to store picture data sets received from the camera 160 and, if present, from the camera 160A. As mentioned above, those picture data sets may be received in the form of a video data stream that is at least temporarily stored for being processed by the processor 114. Such processing may, for example, include pattern recognition to identify (e.g., locate and, optionally, decode) one or more of the features in the received picture data sets.

In the following, exemplary modes of operation of the system 100 as illustrated in FIG. 1A will be discussed in more detail with reference to the remaining drawings. It should be noted that the operational modes discussed herein could also be implemented in a system having a configuration different from that shown in FIG. 1A. The same reference numerals will be utilized to denote the same or similar components.

The system 100 of FIG. 1A is generally operated to provide computer-assistance during a surgical procedure. The computer-assistance may comprise computer-assisted guidance for navigating the surgical device 150, or a part thereof, relative to patient image data acquired by the imaging device 140 and visualized on the display device 120. As stated earlier, such navigation typically requires a preceding registration step, in which a transformation between a navigation reference coordinate system on the one hand and an image coordinate system on the other hand is determined. The navigation reference coordinate system may generally be the body coordinate system of the patient or a tracker coordinate system of a patient tracking device having a fixed position relative to the patient. The patient tracking device may, for example, take the form of a tracker feature arrangement rigidly attached to the patient. The image coordinate system is typically inherently defined in the image data set provided by the imaging device 140.

Figure 2:
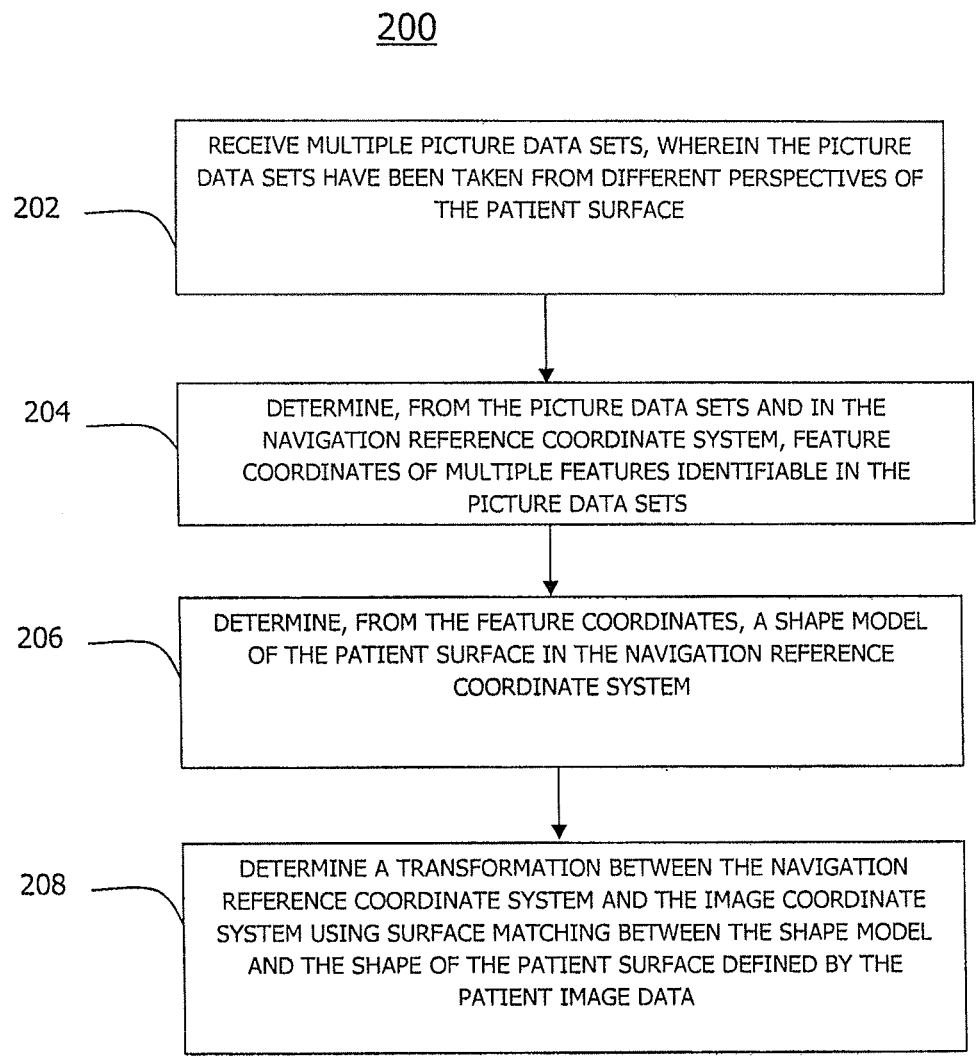
FIG. 2 is a flow diagram illustrating a method embodiment of the technique presented herein.

FIG. 2 illustrates a flow diagram 200 representative of a computer-implemented method embodiment for determining the transformation between the reference coordinate system for navigation of the surgical device 150 and the image coordinate system in which the patient image data acquired by the imaging device 140 are provided.

As illustrated in the flow diagram 200, the method embodiment comprises a first step 202 in which the computing device 110 receives, via the interface 112, multiple picture data sets from one of the camera 160 and the camera 160A shown in FIG. 1A. The picture data sets thus received may at least temporarily be stored in the internal storage 116 for being processed by the processor 114. As stated above, the picture data sets may be received in the form of a continuous video data stream or discontinuously while one or both of the camera 160, 160A are moved with respect to the patient surface of interest. The picture data sets stored in the storage 116 have therefore been taken from two or more different perspectives of the patient surface.

In a following step 204, the processor 114 processes the picture data sets in the storage 116. Using pattern recognition technologies, the processor 114 first identifies (e.g., locates) multiple features in the picture data sets and determines their coordinates (e.g., in the form of their key point coordinates) in a navigation reference coordinate system. In this regard, the processor 114 may also determine the navigation reference coordinate system based on a plurality of the identified features. The processor 114 may have a priori knowledge of the particular features in the picture data sets that span the navigation reference coordinate system, or may simply designate, or select, suitable ones of the identified features to span the navigation reference system.

In a further step 206, the processor 114 determines, from the feature coordinates, a shape model of the patient surface in the navigation reference coordinate system. The shape model may be represented by a point cloud defined by the feature coordinates of features supposed to lie on the patient's skin. The point cloud defining the shape model may typically comprise more than 30 points and may, in certain implementations, comprise several hundred points.

Then, in step 208, the processor 114 determines a transformation (i.e., a set of transformation parameters) between the navigation reference coordinate system and the image coordinate system. That transformation is determined using a surface matching method and between the shape model (e.g., the surface point cloud) determined in step 206 on the one hand and, on the other hand, the shape of the patient surface defined by the patient image data acquired by the imaging device 140. For this purpose, the processor 114 may in a preceding or parallel step not shown in FIG. 2 extract the shape of the patient surface from the patient image data, for example after having retrieved the patient image data from either one of the internal storage 116 and the external storage 130. Once the coordinate system transformation has been determined step 208, the patient image data can be properly registered, using the transformation, with respect to the navigation reference coordinate system in which one or both of the patient and the surgical device 150 is/are tracked for providing image-guided assistance to a surgeon navigating the surgical device 150.

Figure 3:
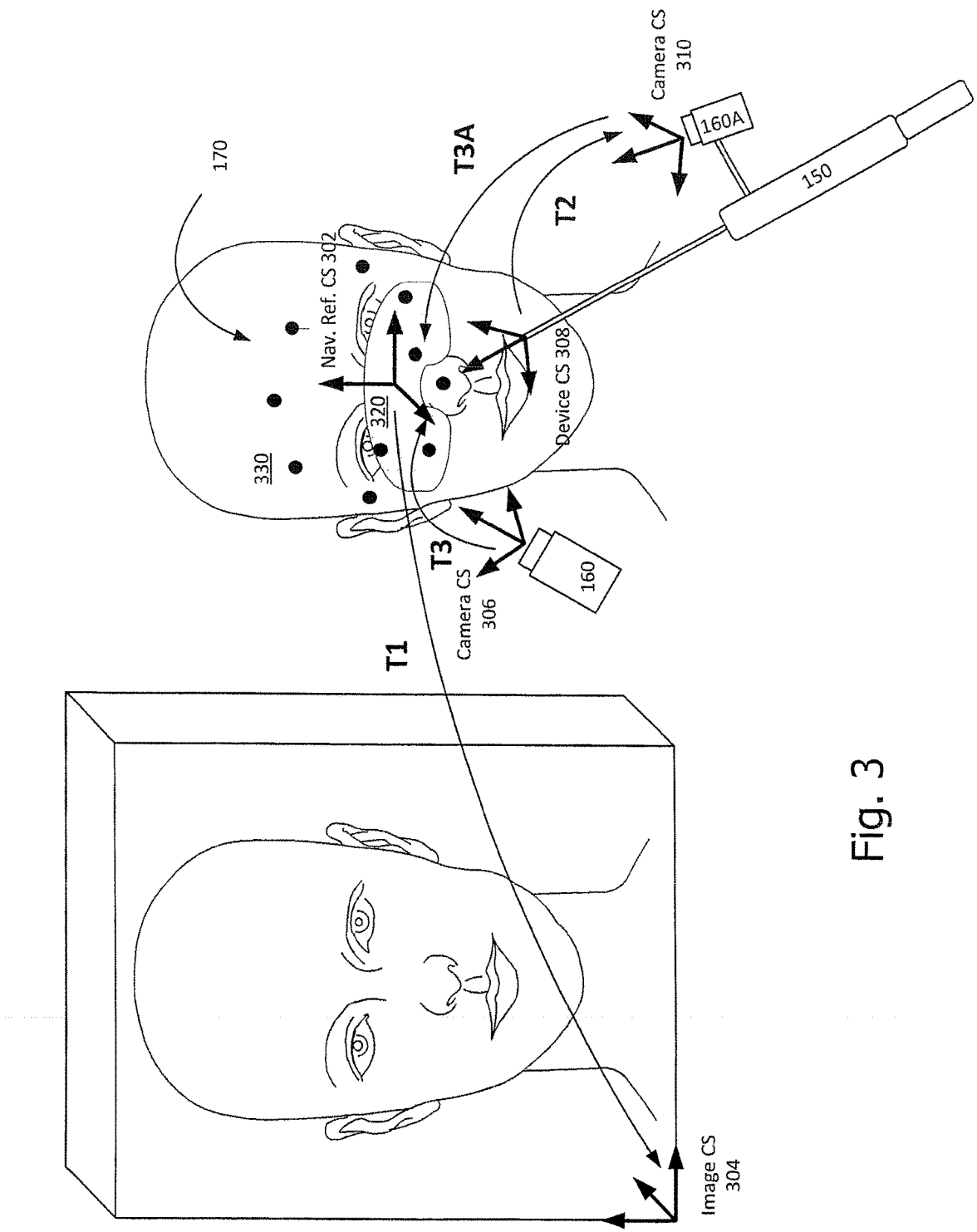
FIG. 3 schematically illustrates registration and navigation scenarios that make use of the system embodiment of FIG. 1A.

FIG. 3 graphically illustrates the transformation, denoted T1, obtained in step 208. As shown in FIG. 3, the transformation T1 establishes a link between the navigation reference coordinate system 302 (that may also be referred to as patient or tracker coordinate system) and the image coordinate system 304. The image coordinate system 304 is in the present case a three-dimensional coordinate system in which pre-operatively acquired image data, or an image volume, of a patient's head are given.

Also shown in FIG. 3 are a handheld, freely moveable registration camera 160 with an associated camera coordinate system 306 and a handheld, freely movable surgical device 150 with an associated device coordinate system 308. As illustrated in FIG. 3, a tracking camera 160A with an associated camera coordinate system 310 is rigidly attached to the surgical device 150. In alternative embodiments, the tracking camera 160A may be mounted in an essentially stationary manner within the operating room. In such embodiments, a separate tool tracking device (not shown) may be rigidly attached to the surgical device 150.

The registration steps 202 to 208 discussed above with reference to FIG. 2 are based on picture data sets acquired by the registration camera 160. The navigation procedure following (an initial) registration procedure, on the other hand, is based on picture data sets received from the tracking camera 160A. As has been explained above, in alternative embodiments, the registration camera 160 could also be attached to the surgical device 150 together with or instead of the tracking camera 160A. In the latter case, the registration camera 160 may also be used for navigation (i.e., tracking) purposes.

As further shown in FIG. 3, the positional relationship between the tracking camera 106A (or, in the alternative embodiments, the camera 160) and the surgical device 150 (e.g., its tip) is defined by transformation parameters of a second transformation T2 between the device coordinate system 308 and the camera coordinate system 310. The corresponding transformation parameters may be derived by a calibration process already during production (e.g., in a factory calibration step for one or both of the surgical device 150 and the respective camera 160/160A) or immediately before the surgical procedure (e.g., using on-site calibration for a universal adaptation to any surgical device 150).

The transformation parameters of the second transformation T2 may be stored as calibration data (e.g., in the internal storage 116 of the computing device 110 shown in FIG. 1A or an internal storage of the respective camera 160, 160A) for use during navigation. Such calibration data may further describe transformation parameters of further transformations between the camera 160 and its associated image coordinate system as well as between the camera 160A and its associated image coordinate system. The corresponding transformation parameters, which might likewise be stored in the internal storage 116, may define a projection model of the respective camera 160, 160A. The projection model may be used to determine the position of the respective camera 160, 160A relative to one or more features identified in a picture data set provided by the respective camera 160, 160A (see, e.g., US 2008/0208041 A1 in this regard). As an example, the projection model may be exploited for registration purposes in connection with step 204 as illustrated in FIG. 2, and, optionally in connection with navigating the surgical device 150 based on picture data sets provided by the tracking camera 160A.

The transformation parameters underlying a particular projection model may be provided by the respective camera manufacturer or by a distributer of the system 100. They could also be estimated with an on-site calibration fixture or be standardized for a particular camera type. In certain implementations, the transformation parameters may be provided via a suitable interface by the respective camera 160, 160A itself (e.g., in real-time dependent on a currently selected zoom level).

Also provided as calibration data, for example in the internal storage 116 of the computing device 110 of FIG. 1A, is information pertaining to the feature set 170 shown in FIG. 3. Such information may include feature relative positions and/or any applied feature coding scheme. Based on the known feature relative positions and the (projected) feature relative positions in an image taken by any one of the cameras 160, 160A (i.e., in the associated camera coordinate system), transformation parameters of a further transformation can be determined (e.g., in real-time) by a perspective back-projection from the corresponding image coordinate system towards any reference system in which the feature coordinates are provided, such as the navigation reference coordinate system 302. This is indicated by third transformations T3 and T3A for cameras 160 and 160A, respectively, in FIG. 3.

The transformation parameters of the third transformation T3 for the camera 160 are calculated by solving the following equation system for each individual feature j:

$$M_{j,160} = T4 \cdot T3^{-1} \cdot M_{j,cal},$$

wherein $M_{j,160}$ is the imaged feature j in a picture of the picture data set (e.g., video frame) of the camera 160 with coordinates relative to its image coordinate system, $M_{j,cal}$ is provided as calibration data and indicative of (e.g., a key point of) the feature j with coordinates relative to the navigation reference coordinate system 302, and a fourth transformation T4 designates the transformation parameters between the camera 160 and its associates image coordinate system.

In a similar manner, the transformation parameters of transformation T3A can be calculated for the tracking camera 160A. It should be noted that the perspective back-projection described above is sometimes also referred to as camera pose estimation, or performed in connection with camera pose estimation.

In the exemplary scenario illustrated in FIG. 3, the feature set 170 is provided in the form of two feature sub-sets, wherein a first feature sub-set is associated with a patient tracking device 320 and a second feature sub-set is associated with a feature patch 330. The second feature sub-set could in addition, or alternatively, be provided in the form of anatomic patient features. In FIG. 3, the individual features are symbolized by black points. Of course, the feature patch 330 could also be generalized by painting an arbitrary or well-defined pattern on the patient's skin.

Figure 4A:
FIGS. 4A, 4B schematically illustrate a feature patch and a surface of a patient tracking device usable in connection with the scenarios of FIG. 3.
Figure 4B:
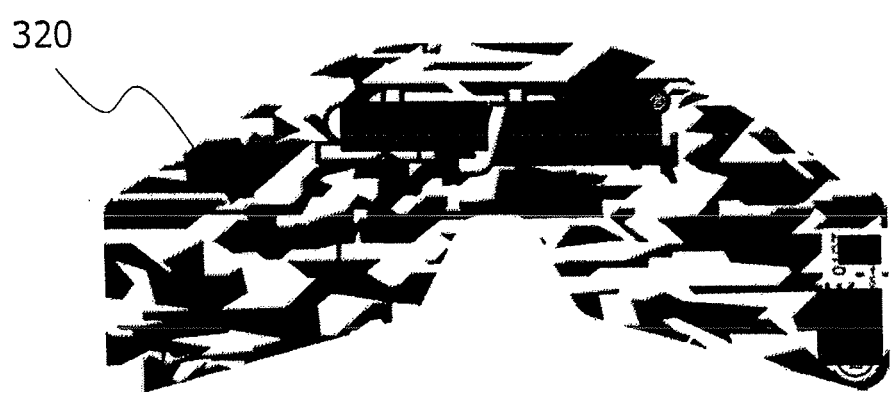

FIG. 4A shows an embodiment of the feature patch 330 of FIG. 3 in the form of a multi-part skin mask that comprises multiple coded features thereon. FIG. 4B shows the two-dimensional (i.e., planar) surface of the patient tracking device 320 of FIG. 3.

With reference to FIG. 4A, the skin mask defining the feature patch 330 comprises a flexible substrate with an adhesive on its side facing the patient and with a printed surface defining robust optically visible features. Each feature has a two-dimensional extension which, in the present embodiment, includes a unique, extended QR-type coding (which permits an overlap of individual features).

In FIG. 4A, an individual extended feature is graphically illustrated to lie within a white ring, wherein the center of the ring defines a feature key point. Generally, each extended feature may define such a specific key point, or a center, that indicates a position, or the coordinates, of the feature. In computer vision, the term feature is also referred to as the description of a key point surrounding (i.e., of a feature extension).

FIG. 4C schematically illustrates the key point concept for an extended feature in the exemplary form of a ring. It will be appreciated that the key point concept can readily be extended to the feature type of FIG. 4A.

It should also be noted that the white ring in FIG. 4A is only used for illustration purposes and not present in the actual feature patch 330. It will also be appreciated that in alternative embodiments the individual features could be defined and coded otherwise. As an example, colored-coded circles or dots may be used.

As said, the substrate of the feature patch 330 shown in FIG. 4A is flexible so as to conform to a patient surface to which the feature patch 330 is applied via its adhesive layer.

In certain implementations, individual features on the feature patch 330 may be grouped within a small area that can be assumed to form a flat (i.e, planar) surface, not affected by any surface bending.

The relative positions of individual features as well as their coding scheme (that allows to differentiate individual features) may be stored as calibration data (i.e., might be known a priori). Also the distance of an individual feature (or feature key point) to the skin of the patient (i.e., the thickness of the feature patch 330) might be stored as calibration data.

FIG. 4B shows the two-dimensional (i.e., planar) surface of the patient tracking device 320 of FIG. 3. In the present embodiment, the patient tracking device 320 is configured as a headset to be seated on a patient's nose. The patient tracking device 320 will be rigidly attached to the patient such that it will move together with the patient. In this way, the patient tracking device 320 can detect any patient movements, which will in particular be required during navigation for tracking or calculating (including estimating) the position of the surgical device 150 or the registration camera 160 relative to the patient in the navigation reference coordinate system 302.

In the present embodiment, that navigation reference coordinate system 302 is defined, or spanned, by features (in the form of combinations of black and white areas) provided on the two-dimensional surface of the patient tracking device of FIG. 4B. This means that once the tracker features defined on the surface of the patient tracking device 320 have been identified and, optionally, decoded in the picture data sets received from any one of the cameras 160, 160A, the navigation reference coordinate system 302 can be determined, together with the coordinates of those features within that coordinate system 302. If features of the feature patch 330 are known within the navigation reference coordinate system 302, they could be used for this calculation, too.

Generally, the above statements regarding the features of the feature patch 330 illustrated in FIG. 4A likewise apply to the features of the patient tracking device 320 of FIG. 4B. For example, the system 100 of FIG. 1A will typically also have a priori knowledge (in the form of calibration data) regarding the relative positions and the codings of the features provided on the patient tracking device 320.

In the following, further embodiments for determining a transformation between the navigation reference coordinate system 302 and the image coordinate system 304 will be described. Those embodiments are, with certain modifications that will be discussed in more detail, derived from the general scenario illustrated in FIG. 3. As will be seen, the coordinate system transformation T1 can be determined without the need of having radio-opaque fiducials or any other markers attached to the patient upon taking the image data by the imaging device 140.

In preparation of the following embodiments, the concept of feature groups, also called "mini trackers" herein, and certain computer vision concepts such as pose estimation, SLAM and SfM will be discussed.

FIG. 4D illustrates the mini tracker concept on an abstract level. A mini tracker is defined by a group of four or, typically, substantially more features and may be regarded as constituting an individual feature of its own (i.e., can be associated with a unique set of three dimensional feature coordinates). In FIG. 4D, four features are depicted. Each feature has a certain extension (indicated by a ring) and coding (indicated by a specific line type). The coding permits to differentiate the four features from each other. It will be appreciated that the abstract mini tracker concept of FIG. 4D may be implemented using the QR-type coding of FIG. 4A or the area coding of FIG. 4B.

The feature group defining the mini tracker permits associating a well-defined point in space (and, optionally, orientation) with the mini tracker. This is illustrated by a coordinate system in FIG. 4D, wherein the origin of the coordinate system ("mini tracker coordinate system") indicates the well-defined point in space and the axes illustrate the orientation. When the feature group is arranged on a surface having a known shape, the origin of the coordinate system can be associated with a known point on that surface. The features of a feature group (i.e., their feature key points) are described within the mini tracker coordinate system or, put another way, the mini tracker coordinate system can be derived from the key point coordinates of the features constituting the feature group. Those key point coordinates may be determined using pose estimation (perspective back-projection) as discussed above with reference to FIG. 3. It should be noted that the mini tracker orientation and the mini tracker coordinate system need not be determined in all embodiments. In many embodiments associating a mini tracker with a well-defined point in space will suffice.

For the feature patch example illustrated in FIG. 4A, it can be assumed that each feature group is arranged on a locally planar surface (which might require arranging the features close to each other) when the feature patch 330 conforms to the patient surface. As such, each mini tracker can be interpreted to define a known surface point (e.g., the origin of the mini tracker coordinate system), and transformations between multiple mini trackers/surface points can be determined as shown in FIG. 4E. Generally, the transformations among several surface points define the relative positions, or coordinates, of the surface points (see step 204 in FIG. 2), and thus a point cloud describing the desired surface model (see step 206 in FIG. 2).

In FIG. 4E the three-dimensional transformation between two exemplary surface points is indicated by $T11^{-1} \cdot T10$. The constituting transformations T10 and T11 associate the respective mini tracker coordinate system with the camera coordinate system (reference numeral 306 in FIG. 3). In one realization, such transformations can be calculated for multiple mini trackers from a single picture data set (e.g., video frame) acquired by the registration camera 160 from a single perspective. In practice, the transformations between surface points (such as $T11^{-1} \cdot T10$) are derived multiple times from multiple picture data sets (taken from multiple perspectives) and then averaged to increase robustness of the calculation.

The transformations T11 and T10 of the surface points relative to the camera coordinate system 306 (see FIG. 3) are in one embodiment calculated using SLAM technologies, including pose estimation. As said, pose estimation relates to determining a position and an (sometimes optional) orientation from a two dimensional picture using a back-projection approach (e.g., as explained above with reference to FIG. 3). SLAM permits a simultaneous localization (i.e., determination of the camera position) and mapping (i.e., reconstruction of the patient surface in the form of the surface model).

SLAM in the present realization models the shape of the patient surface to be reconstructed with local planar areas (defined by the mini trackers), so that the patient surface can locally be reconstructed using planar pose estimation. The pose may in certain embodiments be calculated, for example estimated, relative to a patient tracking device such as the patient tracking device 320 of FIG. 4B (i.e., in the navigation reference coordinate system 302 of FIG. 3). The resulting shape model is represented by a point cloud. As will be appreciated, each point of the point cloud is representative of the feature coordinates of an individual mini tracker (e.g., of the origin of its associated mini tracker coordinate system).

As an alternative to SLAM, a combination of pose estimation and SfM technologies may be used to derive the feature coordinates for the shape model (steps 204 and 206 in FIG. 2). In this regard, an individual feature (e.g., a feature key point, but not necessarily a feature group such as a mini tracker) is identified, in two dimensions, in each of multiple picture data sets acquired by the registration camera 160 from different perspectives. The feature may, in certain embodiments, be provided by the feature patch 330 of FIG. 4A. For each picture data set, the respective camera pose is calculated, for example relative to the patient tracking device 320 of FIG. 4B. As such, there may be a need to differentiate between features on the patient tracking device 320 and features on the feature patch 330.

Then, SfM is applied to derive the three-dimensional feature coordinates (i.e., to reconstruct the patient surface and generated the shape model). SfM builds two-dimensional feature tracks for individual features as the registration camera 160 is moved relative to the patient. From the feature tracks, the feature coordinates are derived in the navigation reference coordinate system (e.g., in the coordinate system 302 of the patient tracking device 320). In this regard, the pose of the registration camera 160 relative to the patient tracking device 320 may be exploited for the picture data sets from which the feature tracks are built. The feature tracks are thus used for three-dimensional feature coordinate reconstruction.

Triangulation and, optionally, bundle adjustment can be applied for the three-dimensional feature coordinate reconstruction and shape model generation. In one variant, triangulation determines for each feature track the two picture data sets (e.g., video frames) with the greatest angular distance in camera poses (e.g., relative to the patient tracking device 320). The two-dimensional feature information is then derived from those two picture data sets to get an initial three-dimensional reconstruction of the feature coordinates in the navigation reference coordinate system. Then, the initial reconstructions for all feature tracks are together with many or all of the associated picture data sets (and associated camera poses) are used to perform a bundle adjustment. Bundle adjustment is an optimization procedure to reduce the reprojection error. Also in the present case the resulting shape model is represented by a point cloud of three-dimensional feature coordinates.

It will be appreciated that SfM can also be performed without explicit camera pose estimation relative to a patient tracking device. The respective camera pose may in such a case be estimated and iteratively optimized. A related process is described by Klein et al., Parallel Tracking and Mapping for Small AR Workspaces, Proceedings of the 2007 6th IEEE and ACM International Symposium on Mixed and Augmented Reality, Pages 1 to 10, 13-16 Nov. 2007.

Based on the above explanations of the tracker concept, pose estimation, SLAM and SfM, more detailed embodiments as depicted in FIGS. 5A to 8B will now be described.

Figure 5A:
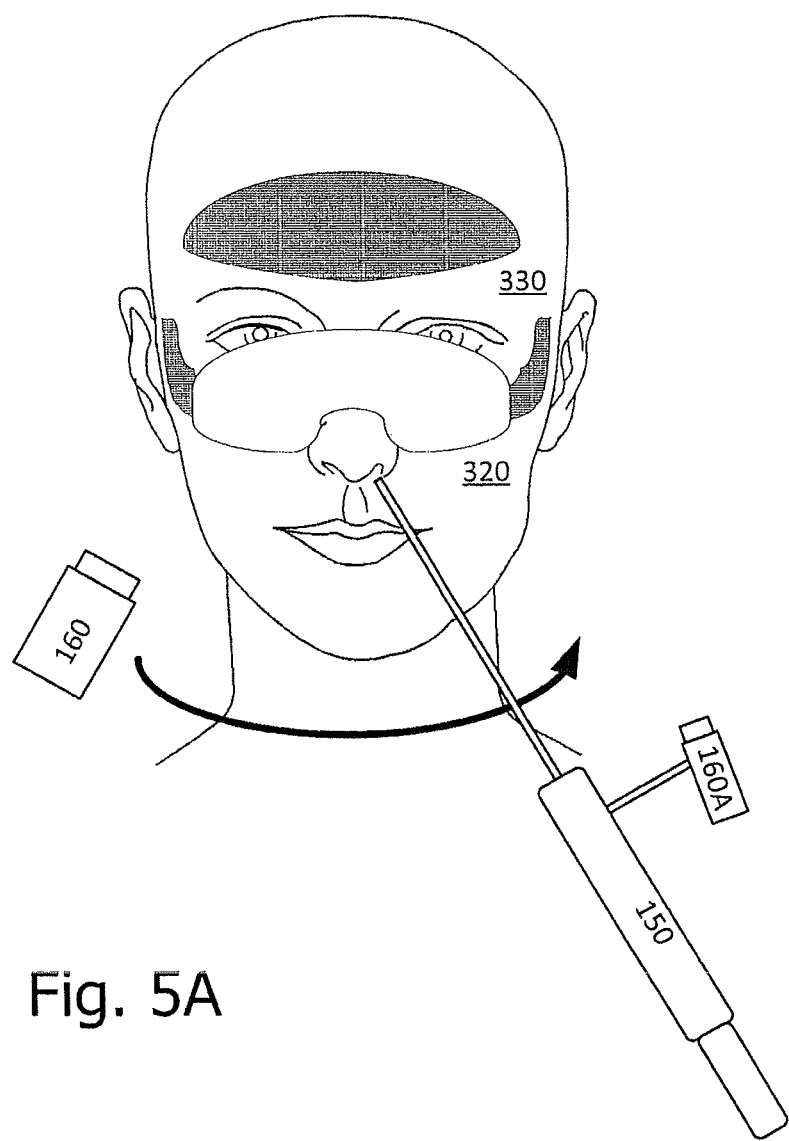
FIGS. 5A-8B illustrate further embodiments of registration and navigation scenarios that make use of the system embodiment of FIG. 1A.
Figure 5B:
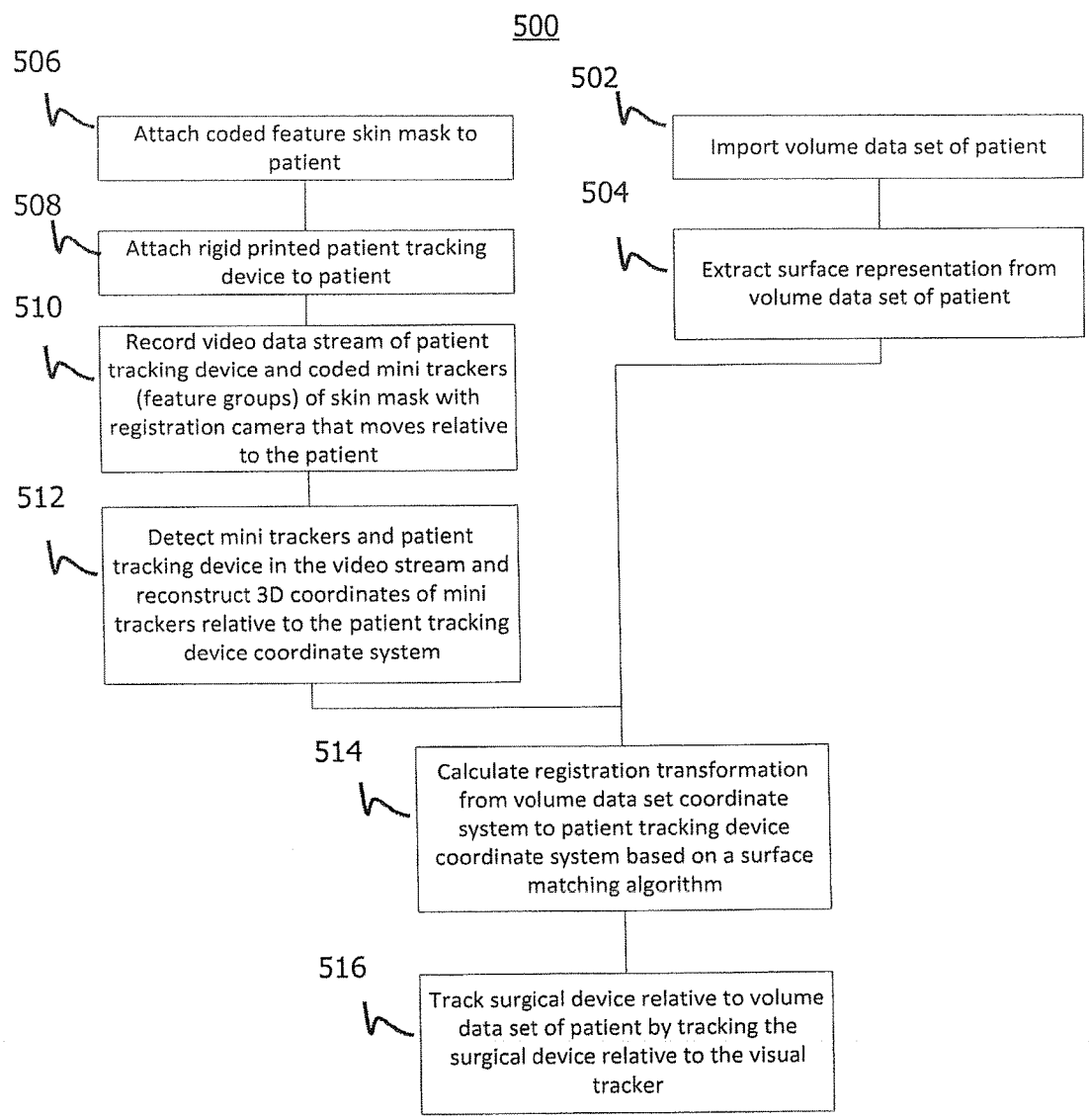
Figure 5C:
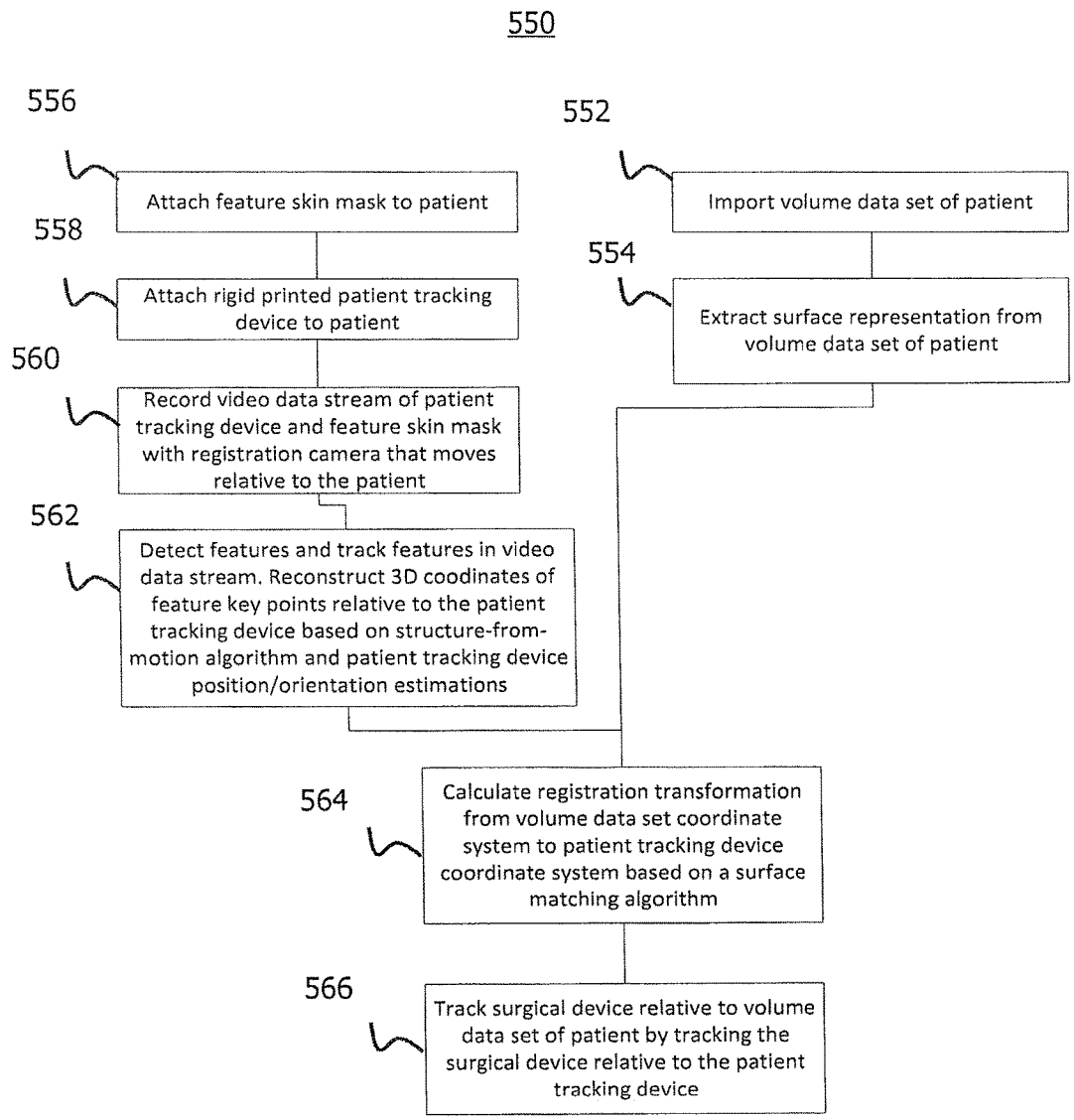

In the embodiments illustrated in FIGS. 5A to 5C, a similar setup as shown in FIG. 3 is used. This means that for registration purposes the handheld camera 160 is moved relative to the patient to provide picture data sets from different perspectives of the patient surface. Both the (multi-part) feature patch 330 of FIG. 4A and the patient tracking device 320 with the feature pattern illustrated in FIG. 4B are applied to the patient. Therefore, both the features of the patient tracking device 320 and the features of the feature patch 330 can be identified in the picture data sets provided by the registration camera 160.

FIG. 5B illustrates a flow diagram 500 of a method embodiment based on the setup of FIG. 5A. The method embodiment makes use of the feature group (or mini tracker) concept illustrated in FIGS. 4C to 4D and pose estimation, but does not require the application of SLAM.

In an initial step 502, the patient region of interest (i.e., that is to be surgically treated) is scanned pre- or intra-operatively. As mentioned above, no specific fiducials or any other markers need to be attached to the patient's anatomy. The resulting patient image data, typically a volume data set, is imported in the computer device 110 of FIG. 1A. This import may be performed using standard protocols such as DICOM.

In a next step 504, the shape of a patient surface of interest is extracted from the image data. The extracted shape representation may describe the skin surface of the anatomic region of interest of the patient. In the exemplary embodiment illustrated in FIG. 5A, the surface of the frontal head and the face is extracted. The extraction may be performed by the computing device 110, or an alternative computing device, using ray tracing techniques or any other technique such as three-dimensional image segmentation.

It will be appreciated that steps 502 and 504 can be performed days or even weeks prior to surgery. In certain cases, both steps could also be performed during (i.e., concurrently with) a surgical treatment.

Immediately before a surgical treatment, the skin mask-type feature patch 330 with the coded features thereon is attached to the skin surface of the patient (step 506). As explained above, the coded features are grouped to form (likewise coded) mini trackers. Due to the adhesive on the side of the feature patch 330 facing the patient, the attached feature patch 330 will conform to the patient surface.

At the same time, the patient tracking device 320 is attached to the patient (step 508). The patient tracking device is attached such that it can be guaranteed that it will not move relative to the patient's anatomy during registration and navigation. In the embodiment illustrated in FIG. 5A, a headset carrying a planar substrate on which tracker features are printed (see FIG. 4B) is used. In alternative embodiments, a headband or headframe may be used or a patient tracking device that can be sticked onto the patient's skin.

The actual registration procedure is started in step 510 with recording, in the internal storage 116 of the computing device 110 of FIG. 1A, a video data stream received from the registration camera 160 while being moved relative to the patient. The corresponding video data stream comprises a continuous series of picture data sets taken from different perspectives relative to the patient surface. The picture data sets permit an identification of the features on both the patient tracking device 320 and the feature patch 330 that are within the respective field of view of the registration camera 160.

Then, in step 512, for each picture data set in which at least four robust features of the patient tracking device 320 can be identified (e.g., detected), the position of each mini tracker on the feature patch 330, that can also be identified in that picture data set, is determined in three dimensions relative the patient tracking device 320 in the navigation reference coordinate system 302 (e.g., using pose estimation as discussed above with reference to FIG. 3). In the present case the navigation reference coordinate system 302 is defined a priori by the identified feature arrangement on the patient tracking device 320 and is determined also in step 512.

As such, step 512 includes estimating the position and orientation (i.e., the pose) of the patient tracking device 320 and the positions of the mini trackers relative to the registration camera coordinate system 306 (in a similar manner as discussed with reference to FIG. 3). By coordinate transformations the positions of the mini trackers in relation to the navigation reference coordinate system 302 can be calculated.

Consequently, by processing the video data stream received from the registration camera 160, the feature coordinates of multiple mini trackers (i.e., of the associated surface points as illustrated in FIG. 4E) relative to the patient tracking device 320 (i.e., in the navigation reference coordinate system 302) can be collected and, optionally, filtered. Filtering may comprise calculating the mean of multiple calculated positions of a single mini tracker as derived from multiple picture data sets (i.e., as taken from different perspectives). As a result, a point cloud indicative of the mini tracker positions (i.e., feature coordinates) on the feature patch 330 relative to the navigation reference coordinate system 320 is obtained. That point cloud is representative of a shape model of the patient surface to which the feature patch has been applied.

One or more of the above calculations can be done while recording the video data stream and providing visual or other feedback to a user operating the registration camera 160. Such feedback may comprise one or more of a rendering of the video data stream acquired by the registration camera 160 on the display device 120, information pertaining to whether or not the patient tracking device 320 can be recognized in the picture data sets, and information pertaining to the status of individual features of the feature patch 330 (e.g., one or more of a detection status, quality information pertaining to the estimated position of the feature, etc.).

After the point cloud indicative of the feature coordinates for the feature patch 330 has been determined in step 512, the method proceeds to step 514. In step 514, surface matching is performed to match the point cloud of feature coordinates in the navigation reference coordinate system 302 as derived in step 512 to the patient surface in the image coordinate system 304 as extracted in step 504 from the image data). Surface matching can be performed using Iterative Closest Points (ICP) or any other technologies. The result of the matching in step 514 is a registration transformation matrix (i.e., transformation parameters) for the transformation T1 from the navigation reference coordinate system 302 (which, in the present embodiment, coincides with the patient tracking device coordinate system) to the image coordinate system 304, or vice versa (see FIG. 3).

Then, in step 516 and based on the registration transformation matrix, the surgical device 150 with the attached tracking camera 160A can be navigated in the patient image volume data set when the navigation camera 160A can identify at least four features known in the navigation reference coordinate system 302 (e.g., features of the patient tracking device 320), and the pose of the tracking camera 160A relative to the patient tracking device 320 can be calculated using pose estimation techniques.

FIG. 5C shows a flow diagram 550 of an alternative approach for determining the coordinate system transformation T1 of FIG. 3 on the basis of the setup illustrated in FIG. 5A. Steps 552 to 566 essentially correspond to steps 502 to 516 discussed above with reference to FIG. 5B, and therefore only the major differences with respect to step 562 will be discussed in more detail. These differences pertain to the fact that the mini tracker concept is not implemented. Instead, SfM technologies with pose estimation are used. Thus, only the individual (coded) features on the feature patch 330 need to be identified and processed.

In step 562, a SfM technique is used to determine the feature coordinates of the features of the feature patch 330. As stated above, SfM refers to the process of estimating three-dimensional structures from two-dimensional sequences of picture data sets. Thus, a three-dimensional surface can be recovered from a (projected) two-dimensional motion field of a moving scene taken by the registration camera 160. In this regard, the individual features of the feature patch 330 are tracked in the sequence of picture data sets (by, e.g., optical flow algorithms) from picture data set to picture data set. By knowing the (e.g., estimated) camera pose relative to the patient tracking device 320 for each picture data set and applying SfM, the three-dimensional coordinates of the identified features in the navigation reference coordinate system 302 (i.e., the patient tracking device coordinate system) can be calculated. The result of those calculations will be a point cloud of coordinates of the features of the feature patch 330 in the navigation reference coordinate system 302.

Figure 6A:
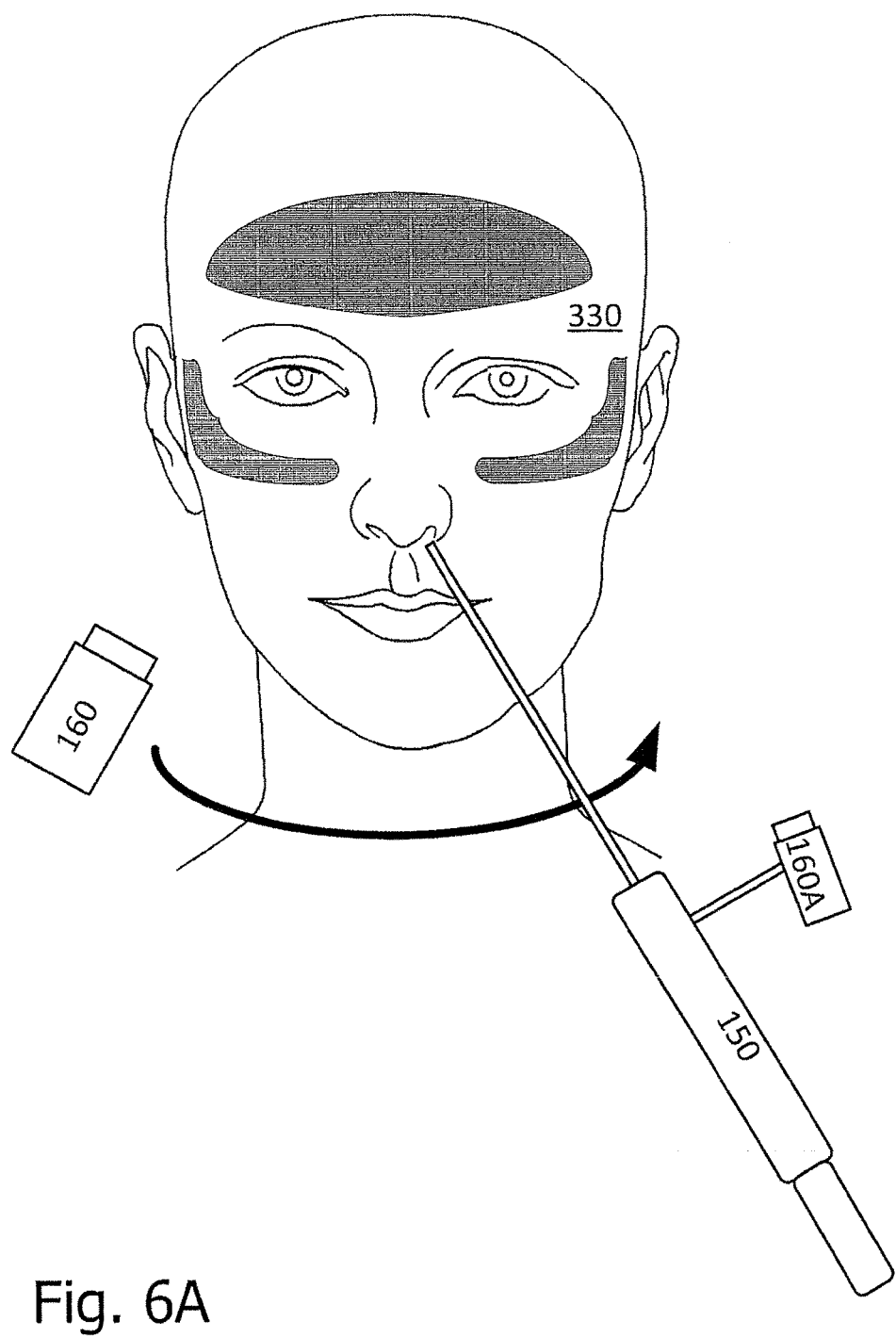

In FIG. 6A an alternative setup is shown in which a dedicated patient tracking device is omitted. Instead of a dedicated patient tracking device pre-attached to the patient (see steps 508 and 558 in FIGS. 5B and 5C, respectively), the computer system 110 generates a patient tracking device from identified features of the feature patch 330 only during the registration procedure.

Figure 6B:
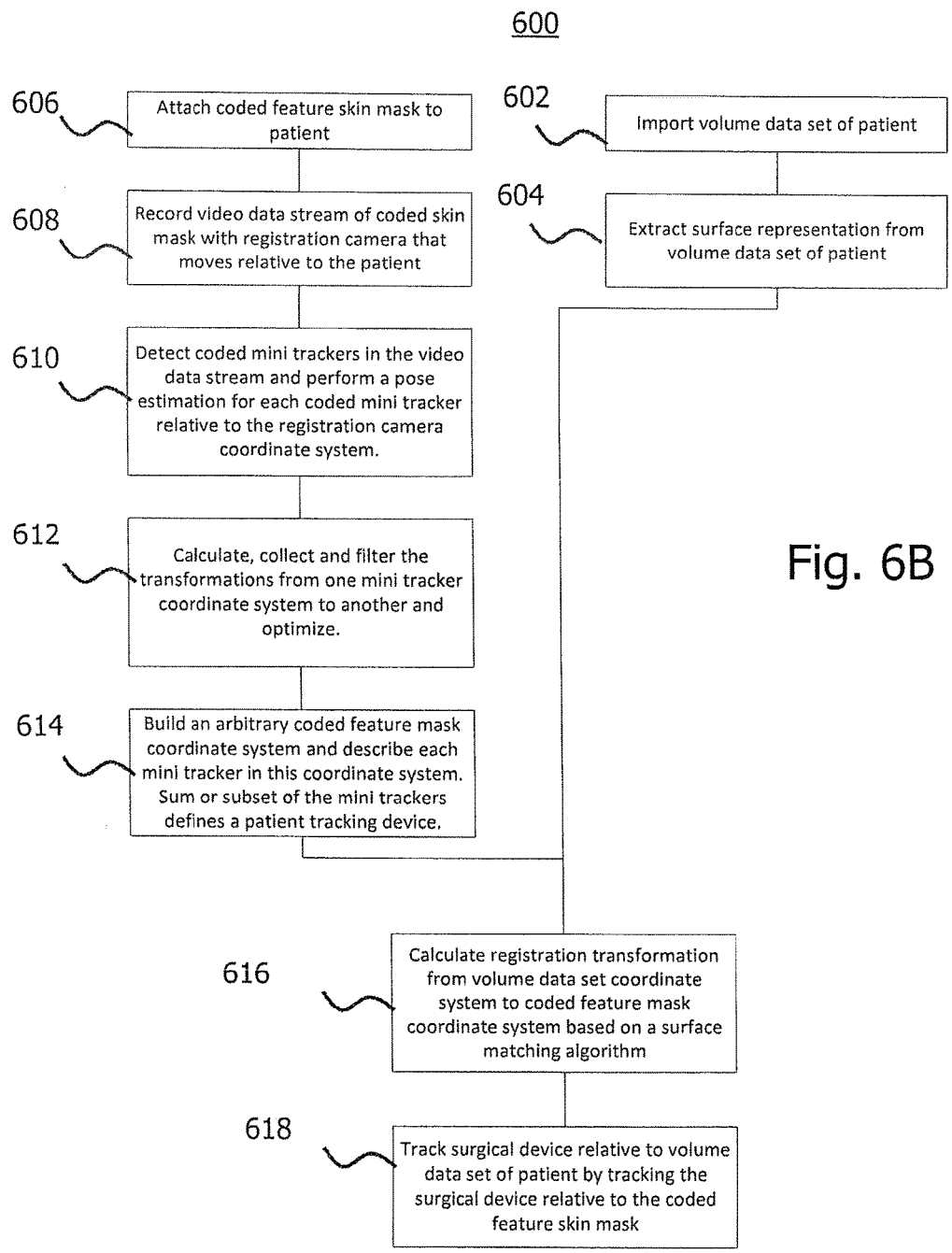

The corresponding processing steps are illustrated in the flow diagram 600 of FIG. 6B. Steps 602, 604, 606, 616 and 618 largely correspond to steps 502, 504, 506, 514 and 516, respectively, as described above with reference to FIG. 5B and will therefore not be discussed in more detail. Accordingly, the method embodiment of FIG. 6B also makes use of the mini tracker concept.

Since no dedicated patient tracking device is attached to the patient, the video data stream recorded in step 608 is only indicative of features of the feature patch 330.

In step 610, for each picture data set, the pose (i.e., position and orientation) of each identified mini tracker of the feature patch 330 relative to the registration camera coordinate system 306 (see FIG. 3) is estimated. As explained above with reference to FIG. 4D, the known position and orientation of a particular mini tracker define a local mini tracker coordinate system. As such, a transformation from the coordinate system of one identified mini tracker to the coordinate system of any other identified mini tracker can be calculated (e.g., in the coordinate system of an arbitrary mini tracker). This process has been explained above with reference to FIG. 4E.

In step 612, the transformations calculated in step 610 for various feature combinations are collected and, optionally, filtered, (e.g., by forming the mean of the transformations for each mini tracker that have been calculated from different perspectives).

Then, in step 614, an arbitrary coordinate system is built from the positions (i.e., coordinates) and/or transformations derived for the identified mini trackers. The feature coordinates of the individual identified mini trackers in the arbitrary "feature patch" coordinate system again form a point cloud (in that coordinate system) representative of a surface model of the patient surface to which the feature patch 330 has been applied. Additionally, multiple one of the identified mini trackers could be designated for later tracking purposes (via the tracking camera 160A) during surgical navigation. As such, the arbitrary feature patch coordinate system is defined to constitute the navigation reference coordinate system 302 that replaces the patient tracking device coordinate system utilized for the same purpose in connection with the method embodiments illustrated in FIGS. 5A to 5C.

Accordingly, the mini trackers may also be used for tracking during navigation to determine the position of the navigation camera relative to the patient (and the surgical device) in step 618. This fact explains the expression mini "trackers". It will be appreciated that in other embodiments in which a dedicated patient tracking device is present (see, e.g., FIG. 5B) the mini trackers need not be used for actual tracking purposes during navigation.

Figure 7A:
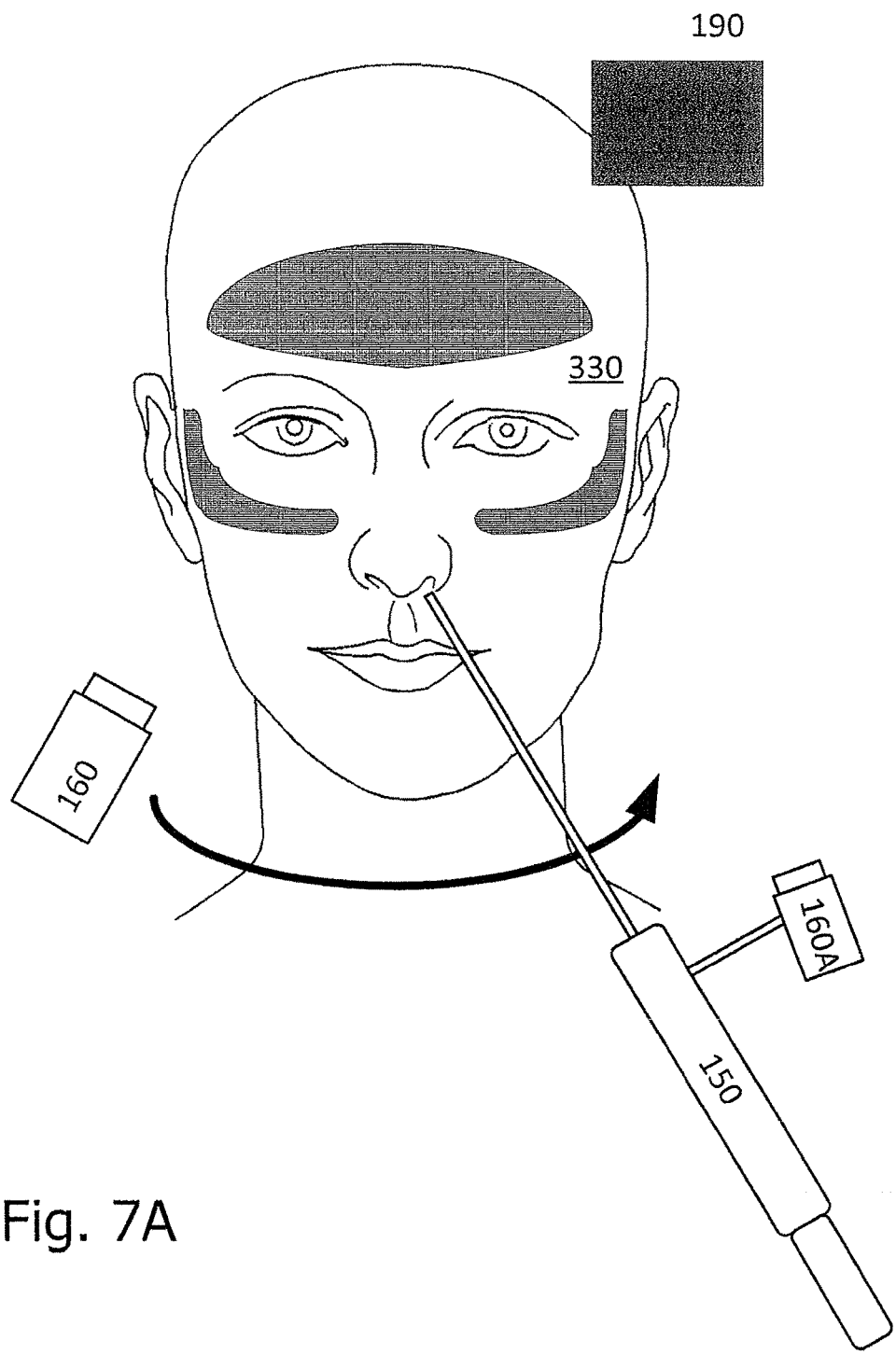

FIG. 7A illustrates a still further setup similar to the setup shown in FIG. 6A but utilizing SfM technologies. As such, the navigation reference coordinate system will not be determined from mini trackers. FIG. 7A also illustrates a supplemental scaling reference 190. In the other embodiments in which mini trackers are used, a priori knowledge about the mini trackers positions may be used for scaling purposes.

The scaling reference 190 of FIG. 7A comprises scaling features having a known relative distance. As an example, the scaling reference 190 may take the form of a planar substrate with a regular or irregular pattern thereon that defines the scaling features. The scaling features are likewise identifiable in the picture data sets provided by the registration camera 160 and permit the determination of a scaling factor for the shape model of the patient surface. In alternative embodiments, such a scaling factor may be derived during the surface matching procedure from a known scaling factor associated with the patient image data taken by the matching device 140.

Figure 7B:
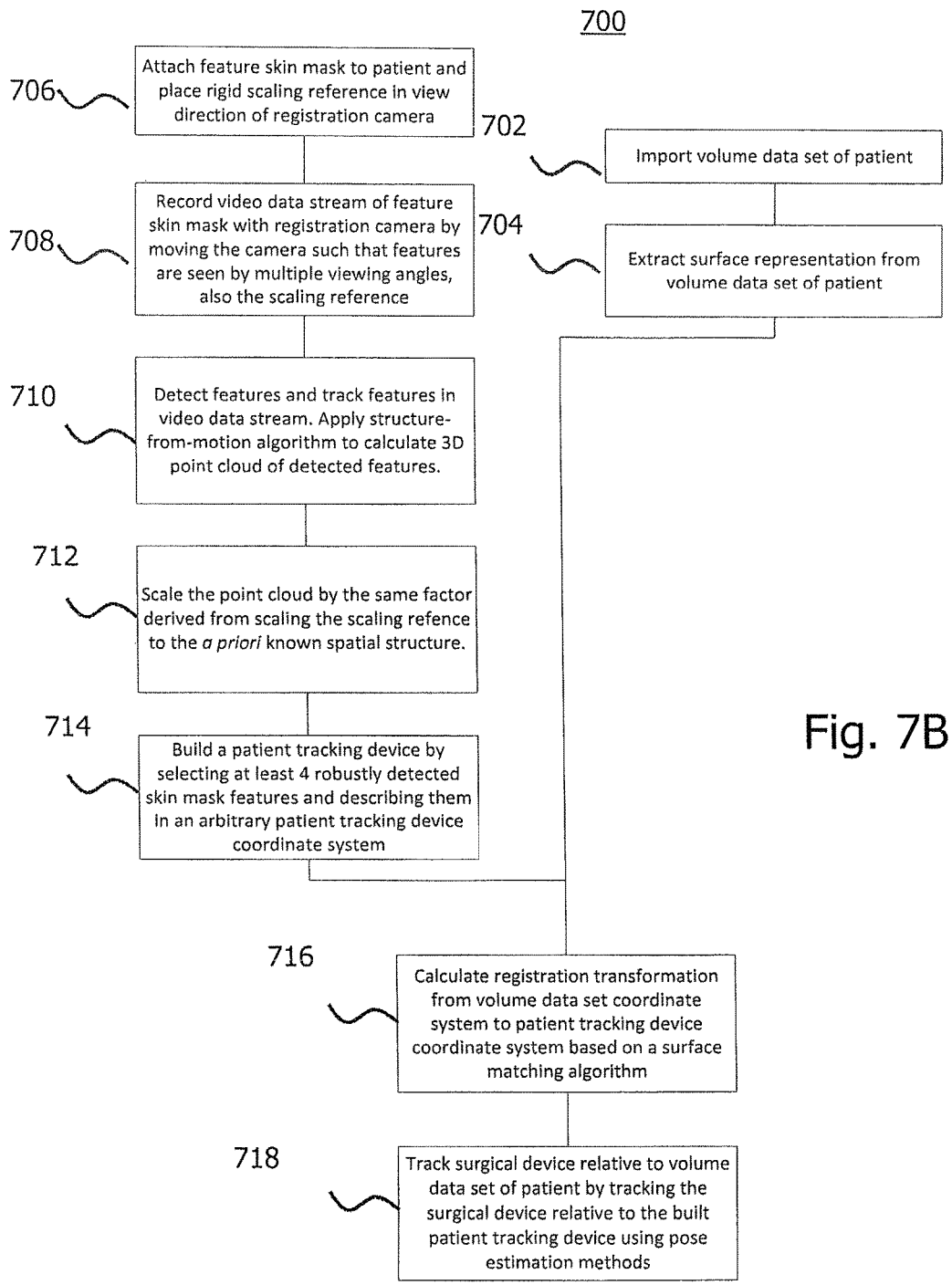

The associated method embodiment illustrated in the flow diagram 700 of FIG. 7B largely corresponds to the method embodiment discussed above with reference to FIG. 6B. According to one difference, the (rigid) scaling reference 190 with at least two robust visually detectable and differentiable optical scaling features, (and a priori known relative position to each other) is included in the video data stream recorded in step 708. It should be noted that the scaling reference 190 can be included in the feature patch 330 if desired. Moreover, the scaling reference 190 need not be attached to the patient, but should have a fixed position to the patient while acquiring the video data stream for registration purposes.

In contrast to step 610, which is performed based, inter alia, on pose estimation, in step 710 SfM is used to calculate a point cloud of the identified (i.e., detected and, optionally, decoded) individual features (not necessarily feature groups). The point cloud is scaled in step 712 by a scaling factor determined from scaling the scaling reference features identified in the picture data sets in accordance with the a priori knowledge of the relative position of the scaling features in space. As will be appreciated, such a scaling is not required for the pose estimation technique utilized in step 610. In step 714 a patient tracking device and an associated coordinate system are built from at least four (individual) features of the feature patch 330. Those at least four features will then be used for estimating the camera pose for navigation purposes in step 718.

Figure 8A:
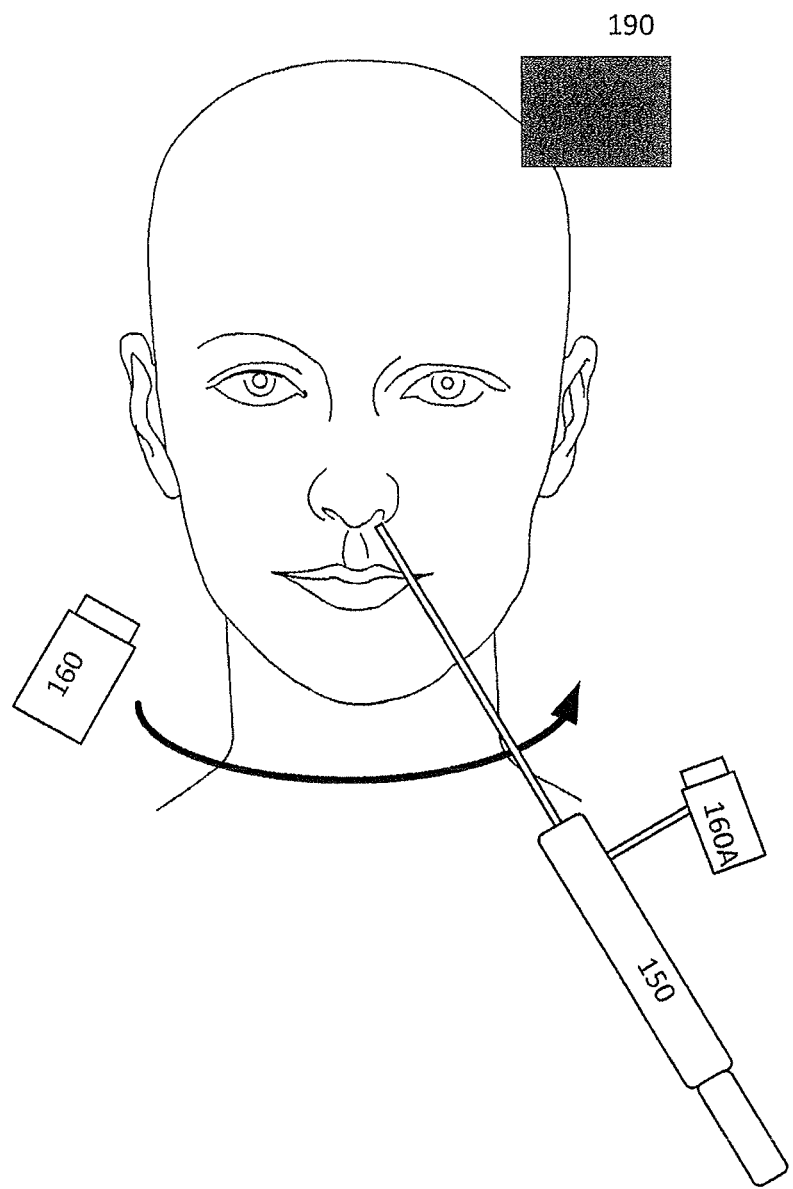
Figure 8B:
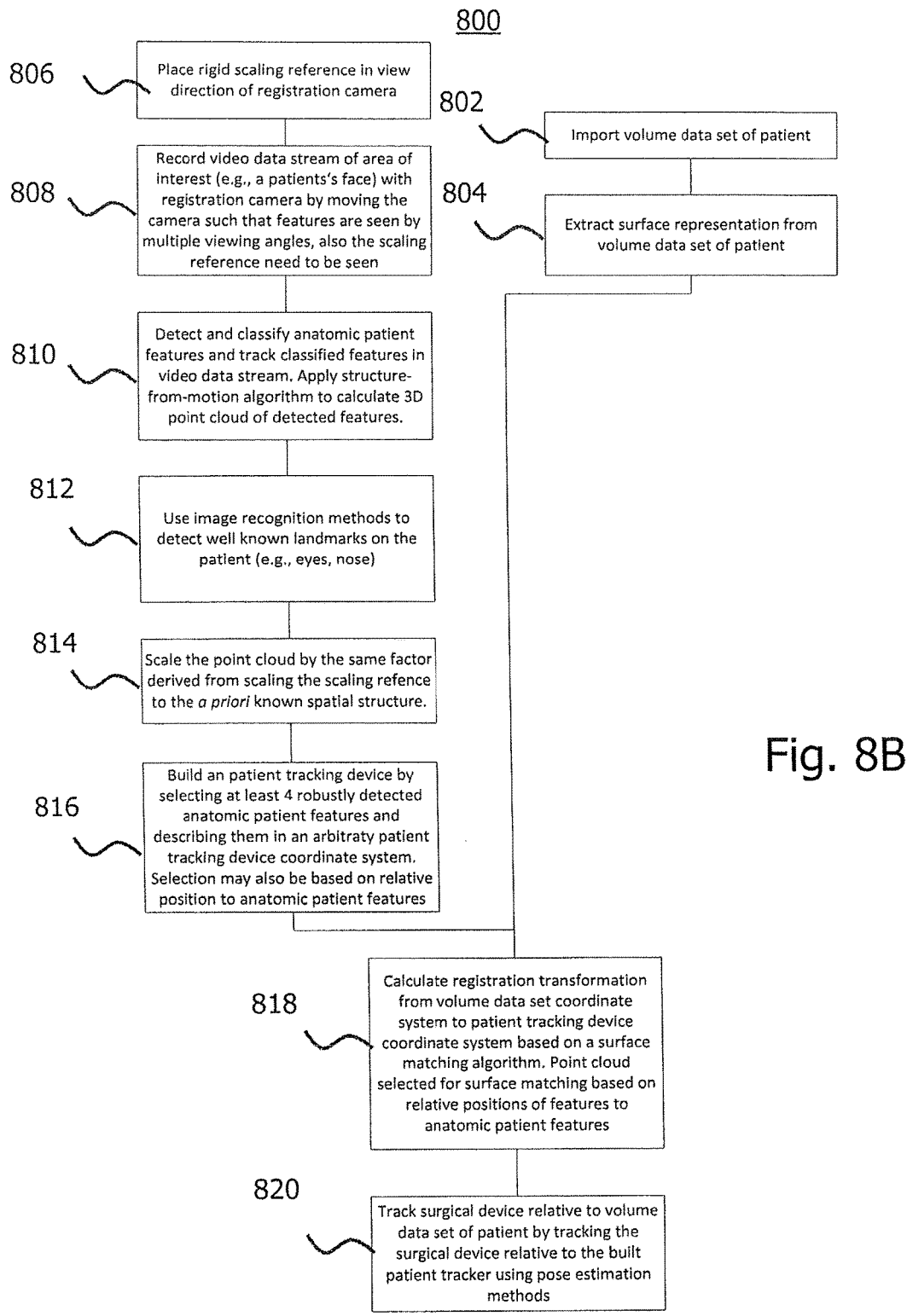

FIG. 8A shows a further setup in which, in addition to the patient tracking device 320 of FIG. 3, also the feature patch 330 has been omitted. On the other hand, an optional scaling reference 190 is again provided. The corresponding method embodiment illustrated in flow diagram 800 of FIG. 8B corresponds in part to the method embodiment of FIG. 7B. As such, a description of steps 802, 804, 814, 816, 818 and 820, which correspond to steps 702, 704, 712, 714, 716 and 718, respectively, will be omitted.

In step 806, the scaling reference 190 is placed in the viewing direction (i.e., in the field of view) of the registration camera 160. Then, in step 808, a video data stream of the patient area of interest (here: the patient's face) is recorded with the registration camera 160 from multiple perspectives, or viewing angles, such that also the scaling reference 190 can be seen. In a further step 810, anatomic patient features are identified and, optionally, classified, for being tracked in the video data stream based on the detected features. SfM is applied to calculate a three-dimensional point cloud as explained above.

In connection with step 810 (i.e., in parallel), pattern recognition is applied in step 812 to identify the additional anatomic patient features (so-called landmarks) which are used to define picture areas where anatomic patient features are expected. This approach may help to prevent detecting features not lying on the patient surface. As will be appreciated, the anatomic patient features will also be utilized to define the patient tracking device for surgical navigation in step 820. As such, neither a dedicated feature patch nor a dedicated patient tracking device is required in the embodiment illustrated in FIGS. 8A and 8B.

In the implementation of FIG. 8A, the anatomic patient features used in step 810 may be personal skin features. Such skin features include one or more of pores, freckles and birth marks detectable (via pattern recognition) in the picture data sets acquired by the registration camera 160. It will be appreciated that in other implementations a pattern painted on the patient's skin may be used for the same purpose as the skin features. Generally, such a painted pattern may replace the substrate-based feature patch 330 in any of the above embodiments.

It should be noted that in the setup illustrated in FIG. 8A the scaling reference 190 is optional. As an alternative, scaling can be performed in connection with surface matching based on scaling information inherently included in the patient image data.

As has become apparent from the above embodiments, the present disclosure provides a surgical navigation technique with innovative registration approaches. The navigation system can be provided at low costs since, in the simplest variant, a single camera (e.g., a web cam coupled to a computer device via an interface) is sufficient. The registration procedure is easy and intuitive, and does not require any particular patient treatment for the acquisition of the patient image data for surgical navigation.

In the foregoing, principles, embodiments and various modes of implementing the technique disclosed herein have exemplarily been described. The present invention should not be construed as being limited to the particular principles, embodiments and modes discussed herein. Rather, it will be appreciated that various changes and modifications may be made by a person skilled in the art without departing from the scope of the present invention as defined in the claims that follow.

The invention claimed is:

1. A system for determining a transformation between a navigation reference coordinate system for navigation of a surgical device relative to patient image data and an image coordinate system in which the patient image data define a shape of a patient surface of a patient, the system comprising:

a first camera movable relative to the patient upon taking picture data sets from different perspectives;

an interface adapted to receive the picture data sets from the first camera, wherein the first camera is a video camera and the picture data sets are received from the video camera in the form of a video data stream; and a processor adapted to determine, from the picture data sets and in the navigation reference coordinate system, feature coordinates of multiple features identifiable in the picture data sets, to determine, from the feature coordinates, a shape model of the patient surface in the navigation reference coordinate system, and to determine a transformation between the navigation reference coordinate system and the image coordinate system using surface matching between the shape model and the shape of the patient surface defined by the patient image data.

2. A device for determining a transformation between a navigation reference coordinate system for navigation of a surgical device relative to patient image data and an image coordinate system in which the patient image data define a shape of a patient surface, the device comprising:

an interface adapted to receive multiple picture data sets from a first camera movable relative to the patient upon taking the picture data sets from different perspectives of the patient surface, wherein the first camera is a video camera and the picture data sets are received from the video camera in the form of a video data stream; and a processor adapted to determine, from the picture data sets and in the navigation reference coordinate system, feature coordinates of multiple features identifiable in the picture data sets, to determine, from the feature coordinates, a shape model of the patient surface in the navigation reference coordinate system, and to determine a transformation between the navigation reference coordinate system and the image coordinate system using surface matching between the shape model and the shape of the patient surface defined by the patient image data.

3. A method of determining a transformation between a navigation reference coordinate system for navigation of a surgical device relative to patient image data and an image coordinate system in which the patient image data define a shape of a patient surface, the method comprising:

receiving multiple picture data sets from a first camera movable relative to the patient upon taking the picture data sets from different perspectives of the patient surface, wherein the first camera is a video camera and the picture data sets are received from the video camera in the form of a video data stream;

determining, from the picture data sets and in the navigation reference coordinate system, feature coordinates of multiple features identifiable in the picture data sets;

determining, from the feature coordinates, a shape model of the patient surface in the navigation reference coordinate system; and determining a transformation between the navigation reference coordinate system and the image coordinate system using surface matching between the shape model and the shape of the patient surface defined by the patient image data.

4. The method of claim 3, wherein
the first camera is at least one of a handheld camera and attachable to the surgical device.

5. The method of claim 3, wherein
several of the features identifiable in at least one picture data set are grouped to form a feature group, wherein at least one of a position and orientation is attributable to each feature group.

6. The method of claim 3, wherein
at least one of the feature coordinates and the shape model is determined using one or more of a structure-from-motion technique, a simultaneous localization and mapping technique, and a pose estimation technique.

7. The method of claim 6, wherein
at least one of the feature coordinates and the shape model is determined using a simultaneous localization and mapping technique; and wherein
simultaneous localization and mapping technique is applied to the feature groups.

8. The method of claim 7, wherein
the structure-from-motion technique builds feature tracks for individual features identifiable in the picture data sets from different perspectives and triangulation based on different perspectives is applied to individual feature tracks.

9. The method of claim 3, wherein
the shape model is represented by a point cloud.

10. The method of claim 3, further comprising
determining the navigation reference coordinate system on the basis of at least some of the features identified in the picture data sets.

11. The method of claim 3, wherein
the feature coordinates are determined for one or more tracker features of a patient tracking device for use during surgical navigation, wherein the patient tracking device is at least partially identifiable in the picture data sets and has a fixed position relative to the patient.

12. The method of claim 3, wherein
the feature coordinates are determined for one or more tracker features of a patient tracking device for use during surgical navigation, wherein the patient tracking device is at least partially identifiable in the picture data sets and has a fixed position relative to the patient; and wherein
the tracker features at least partially define the navigation reference coordinate system.

13. The method of claim 3, wherein
the feature coordinates are determined for one or more anatomic patient features identifiable in the picture data sets.

14. The method of claim 13, further comprising
identifying the one or more anatomic patient features in the picture data sets using generic knowledge about anatomic features.

15. The method of claim 13, wherein
several of the features identifiable in at least one picture data set are grouped to form a feature group, wherein at least one of a position and orientation is attributable to each feature group; wherein
at least one of the feature coordinates and the shape model is determined using a simultaneous localization and mapping technique; wherein
simultaneous localization and mapping is applied to the feature groups; and wherein
the navigation reference coordinate system is at least partially determined from the anatomic patient features.

16. The method of claim 13, wherein
the shape model is at least partially determined from the anatomic patient features.

17. The method of claim 3, wherein
the feature coordinates are determined for one or more patch features of a feature patch applied to the patient and at least partially identifiable in the picture data sets.

18. The method of claim 17, wherein
the method further comprises determining the navigation reference coordinate system on the basis of at least some of the features identified in the picture data sets; and wherein
the navigation reference coordinate system is at least partially determined from the patch features.

19. The method of claim 17, wherein
the feature patch conforms to the patient surface and wherein the shape model is at least partially determined from the patch features.

20. The method of claim 3, further comprising
deriving a scaling factor from the surface matching, and wherein the navigation reference coordinate system is determined also from the scaling factor.

21. The method of claim 3, wherein
in the picture data sets scaling features of a scaling reference are identifiable, and wherein the navigation reference coordinate system is determined also from a scaling factor derived from the scaling features.

22. The method of claim 3, further comprising
tracking or calculating, during navigation, a position of the surgical device, or a portion thereof, relative to the navigation reference coordinate system, which has been determined from one or more of the features.

23. The method of claim 22, wherein
the tracking or calculating is performed based on at least of one or more patient features and one or more tracker features of the patient tracking device, wherein the patient tracking device is different from a feature patch applied to the patient.

24. The method of claim 22, further comprising
visualizing the surgical device or a portion thereof relative to the patient image, wherein the visualization is adapted in accordance with the tracking or calculating.

25. The method of claim 22, wherein
the picture data sets are received from a first camera and wherein the tracking or calculating is performed based on picture information provided by a second camera different from the first camera.

26. The method of claim 25, wherein
the second camera is maintained at an essentially fixed location in an operating room during surgery.

27. The method of claim 22, wherein
the picture data sets are received from a first camera and wherein the tracking or calculating is also performed based on the picture data sets received from the first camera.

28. The method of claim 3, wherein
two or more of the features identifiable in the picture data sets are coded according to a pre-defined coding scheme so as to be differentiable from each other in the picture data sets.

29. The method of claim 3, further comprising
identifying one or more of the features in the picture data sets based on pattern recognition.

30. The method of claim 3, further comprising
receiving the patient image data, the patient image data being provided in the image coordinate system; and
extracting the shape of the patient surface from the patient image data.

31. The method of claim 30, wherein
the patient image data do not show any registration marker.

32. The method of claim 30, wherein
the patient image data are generated pre-operatively.

33. The method of claim 3, wherein
the transformation is determined prior to navigation and additionally one or more times during navigation to verify or correct the transformation determined prior to navigation.

34. The method of claim 33, wherein
the transformation is determined anew based on each picture data set received during navigation.

* * * * *

UNITED STATES PATENT AND TRADEMARK OFFICE
CERTIFICATE OF CORRECTION

PATENT NO. : 9,901,407 B2  
APPLICATION NO. : 14/905690  
DATED : February 27, 2018  
INVENTOR(S) : Jochen Breisacher et al.

Page 1 of 1

It is certified that error appears in the above-identified patent and that said Letters Patent is hereby corrected as shown below:

On the Title Page

Item (71) the Applicant Information currently reads:  
STRYKER LEIBINGER GMBH & CO KG  
Should read:  
Stryker European Holdings I, LLC Signed and Sealed this  
Twenty-fifth Day of September, 2018

Andrei Iancu  
*Director of the United States Patent and Trademark Office*